United States Patent [19]
Takagawa et al.

[11] Patent Number: 5,948,949
[45] Date of Patent: *Sep. 7, 1999

[54] PROCESS FOR PRODUCING 2,6-DIMETHYLNAPHTHALENE

[75] Inventors: Makoto Takagawa; Ryusuke Shigematsu, both of Tsukuba; Kuniaki Ageishi; Ko Kedo, both of Kurashiki, all of Japan

[73] Assignee: Mitsubishi Gas Chemical Company, Inc., Tokyo, Japan

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/777,078

[22] Filed: Dec. 30, 1996

[30] Foreign Application Priority Data

| Feb. 28, 1996 | [JP] | Japan | 8-041232 |
|---|---|---|---|
| Mar. 15, 1996 | [JP] | Japan | 8-059739 |
| Mar. 15, 1996 | [JP] | Japan | 8-059741 |
| Apr. 12, 1996 | [JP] | Japan | 8-091522 |
| Apr. 12, 1996 | [JP] | Japan | 8-091523 |

[51] Int. Cl.$^6$ .................. C07C 5/22; C07C 7/14
[52] U.S. Cl. ............ 585/817; 585/477; 585/478; 585/479; 585/812; 585/813; 585/814; 585/816; 585/817
[58] Field of Search .................. 585/477, 478, 585/474, 480, 481, 812, 813, 814, 816, 817

[56] References Cited

U.S. PATENT DOCUMENTS

| 3,541,175 | 11/1970 | Hedge . | |
|---|---|---|---|
| 3,590,091 | 6/1971 | Skarada et al. | 260/674 |
| 3,649,708 | 3/1972 | Schroeder et al. | 260/674 N |
| 3,888,938 | 6/1975 | Ogasawara et al. | 260/668 A |
| 3,957,896 | 5/1976 | Yokoyama et al. | 260/668 A |
| 4,900,717 | 2/1990 | Holtmann et al. | 585/812 |

FOREIGN PATENT DOCUMENTS

WO 95/18086  7/1995  WIPO .

OTHER PUBLICATIONS

Shima, T. et al., "Refining 2,6–dimethylnaphthalene", *Chemical Abstracts*, vol. 84, No. 5, abstract No. 30750w, 1976, abstract of JP 50–022553.
Shima, T. et al., "Refining 2,6–dimethylnaphthalene", *Chemical Abstracts*, vol. 84, No. 1, abstract No. 4734z, 1976, abstract of JP 50–017063.
Derwent Abstract of JP 48 005 767 of Teijin Ltd., Jan. 24, 1993, Database WPI, Week 7334, Derwent PUblications Ltd., London, GB.
*Patent Abstracts of Japan*, vol. 13, No. 095, Mar. 6, 1989 of JP 63–275528, Nov. 14, 1988.
*Derwent Publications*, AN74–73533V of JP 49–070952, Jul. 9, 1974.
O. –A. Neumüller, Basis–Römpp, Taschen–Lexikon der Chemie ihrer Randgebiete und Hilfswissenschaften, pp. 279–280, Franckh'sche Germany Verlagshandlung, Stuttgart, 1977.

*Primary Examiner*—Glenn Caldarola
*Assistant Examiner*—Thuan D. Dang
*Attorney, Agent, or Firm*—Frishauf, Holtz, Goodman, Langer & Chick, P.C.

[57] ABSTRACT

A process for producing highly pure 2,6-dimethylnaphthalene in a high yield from a mixture of dimethylnaphthalene isomers in the presence of a solvent, such as an aliphatic or alicyclic saturated hydrocarbon. Highly pure 2,6-dimethylnaphthalene can be produced steadily for a long time by filtering the 2,6-dimethylnaphthalene crystal precipitated by the crystallizing by using a filtration apparatus, such as a rotary vacuum filter, peeling-off the filtered cake from a filter cloth and cleaning the filter cloth with a solvent, at a temperature not lower than a filtration temperature.

18 Claims, No Drawings

PROCESS FOR PRODUCING 2,6-DIMETHYLNAPHTHALENE

BACKGROUND OF THE INVENTION

1. Field of the Invention

The present invention relates to a process for producing 2,6-dimethylnaphthalene and a process for producing a 2,6-naphthalenedicarboxylic acid. More particularly, it pertains to a process for producing highly pure 2,6-dimethylnaphthalene which is useful as a starting raw material for a 2,6-naphthalenedicarboxylic acid and the like in a high recovery rate in an industrially advantageous manner by means of an crystallization treatment for the mixture of dimethylnaphthalene isomers, and a process for producing a 2,6-naphthalenedicarboxylic acid from the 2,6-dimethylnaphthalene obtained by the aforesaid process which acid is useful as a starting raw material for a high performance polyester and the like.

2. Description of the Related Art

It has heretofore been known that a 2,6-naphthalenedicarboxylic acid and an ester thereof are each a compound of industrial importance as a starting raw material for a high performance polyester which is employed for the production of polyethylene naphthalate in the form of fiber, film and the like that is excellent in tensile strength and heat resistance.

The 2,6-naphthalenedicarboxylic acid and an ester thereof that are used for such a purpose are required to be highly pure and besides 2,6-dimethylnaphthalene (hereinafter dimethylnaphthalene is sometimes abbreviated to "DMN") which is used as a starting raw material thereof is required to be also highly pure because of the reasons described hereunder.

Specifically, 2,6-DMN, when being low in purity, causes the impurities contained therein to be oxidized or esterified, and eventually lowers the purity of a 2,6-naphthalenedicarboxylic acid and an ester thereof when being produced therefrom. A part of the impurities that are formed during the steps of oxidation and esterification, originating from the impurities in 2,6-DMN is extremely difficult to remove, thereby making it also extremely difficult to obtain a 2,6-naphthalenedicarboxylic acid or a dimethyl 2,6-naphthalenedicarboxylate each having high purity. In addition, such impurities, when being present in 2,6-DMN, deteriorates not only the purity of the above-mentioned acid and ester, but also the yield thereof based on 2,6-DMN to a remarkable extent. It is therefore, indispensable that highly pure 2,6-DMN be obtained in order to produce a 2,6-naphthalenedicarboxylic acid and a dimethyl 2,6-naphthalenedicarboxylate under industrially advantageous conditions. DMN has 10 isomers according to the positions of two methyl groups. Accordingly, 2,6-DMN as a starting raw material for a 2,6-naphthalenedicarboxylic acid is required to be a highly pure product substantially free from any of the isomers other than 2,6-DMN.

It being so, 2,6-DMN as a starting raw material for oxidation is desired to be highly pure as much as possible. In order to enhance the purity of 2,6-DMN, however, the burden imposed on its purification is increased. Hence, the purity of 2,6-DMN as a starting raw material for oxidation should be determined taking into consideration such factors as the burden on its purification, relation between the DMN purity and the result of the oxidation reaction, influence of its purity on the purity of the oxidation product and, in the case of purifying as a dimethyl 2,6-naphthalenedicarboxylate, relation between the DMN purity and the result of the methyl-esterification reaction and the burden on purifying the methyl ester in addition thereto. It is usually necessary to set the purity of 2,6-DMN on a high level of at least 98.0%, comprehensively taking these factors into consideration.

As the process for producing 2,6-DMN, there are available for example, a process in which 2,6-DMN is isolated from a tar fraction or a petroleum fraction, a process in which naphthalene or methylnaphthalene is methylated, succeedingly isomerized and separated and the like processes. Since the fractions and isomerization reaction products contain almost all of the 10 kinds of isomers, 2,6-DMN needs to be isolated from the mixture of a lot of isomers.

On the other hand, Japanese Patent Application Laid-Open Nos. 134634/1974, 8935/1975, 76852/1973 and 129534/1975 disclose a process for producing o-tolylpentene-2 in high yield from o-xylene and butadiene; a process for producing 1,5-dimethyltetralin by cyclizing o-tolylpentene-2; a process for producing 1,5-DMN in high yield and in high selectivity by dehydrogenating 1,5-dimethyltetralin; and a process for producing a mixture of isomers consisting essentially of 1,5-1,6- and 2,6-DMNs by isomerizing 1,5-DMN. Accordingly, by combining the above-mentioned processes it is made possible to produce a mixture of isomers consisting essentially of 1,5-, 1,6- and 2,6-DMNs from o-xylene and butadiene. Thus, there is made avialable a process for producing 2,6-DMN by isolating 2,6-DMN from the aforesaid mixture.

As described hereinbefore, any of the processes for producing 2,6-DMN that have heretofore been avialable makes it necessary to isolate 2,6-DMN from the mixture of isomers to recover the same. However, it is extremely difficult to purify 2,6-DMN by means of distillation which is frequently applied to the separation and purification of ordinary organic compounds, since 10 kinds of isomers have each a boiling point very close to one another as shown hereunder together with the melting point.

|         | Boiling point (° C.) | Melting point (° C.) |
|---------|----------------------|----------------------|
| 1,5-DMN | 269                  | 82                   |
| 1,6-DMN | 266                  | −16                  |
| 2,6-DMN | 262                  | 112                  |
| 1,7-DMN | 263                  | −14                  |
| 1,8-DMN | 270                  | 65                   |
| 2,7-DMN | 262                  | 98                   |
| 1,3-DMN | 265                  | −4.2                 |
| 1,4-DMN | 265                  | 6                    |
| 2,3-DMN | 269                  | 104                  |
| 1,2-DMN | 271                  | −3.5                 |

As is clear from the table, 2,6-DMN has a highest melting point of all the DMN isomers. On the other hand, it is known that 2,6-DMN forms a eutectic together with at least one of 1,5-DMN, 2,7-DMN and 2,3-DMN. It is therefore, necessary that the ratio by amount of 2,6-DMN in the isomer mixture to the isomers be more than the compositional ratio of the eutectic in order to precipitate 2,6-DMN as a crystal by means of crystallization from the mixture of the isomers. That is to say, the condition under which 2,6-DMN is at first precipitated as a crystal by cooling is that the molar ratios of 1,5-DMN, 2,7-DMN and 2,3-DMN each in the mixture of the isomers to 2,6-DMN in the same are not more than 1.9, 1.4 and 1.1, respectively.

As a method for isolating 2,6-DMN from the mixture of the isomers, there are proposed a crystallization method, an adsorption method, a method in which 2,6-DMN is caused to form a complex by the use of a certain kind of an organic compound, the resultant complex is separated and then it is decomposed to recover 2,6-DMN, and the like methods. Of these methods, crystallization method is most simple, convenient and suitable as an industrial isolation method.

In particular, in the case of producing a mixture of isomers consisting essentially of 1,5-, 1,6- and 2,6-DMN from o-xylene and butadiene as starting materials and isolating 2,6-DMN therefrom, a crystallization method is effective because of the comparatively small number of isomers in the starting raw material to be purified. In the case of methylating naphthalenes, isomerizing the reaction product and isolating 2,6-DMN or in the case of isolating the same from a tar fraction or a petroleum fraction, the combination of an adsorption method and a crystallization method is usually employed, since 2,6-DMN needs to be isolated from the mixture of a large number of isomers.

It is well known that in the case of isomerizing DMN, isomerization between adjacent β-positions and isomerization of methyl-migration from one ring to another are unlikely to take place as compared with that between α-position and β-position. Specifically, the above-mentioned 10 DMN isomers are classified into four groups, namely A to D groups as undermentioned with regard to isomerization, and isomerization among different groups is unlikely to take place as compared with that in the same group.

Group A—1,5-DMN, 1,6-DMN, 2,6-DMN
Group B—1,8-DMN, 1,7-DMN, 2,7-DMN
Group C—1,4-DMN, 1,3-DMN, 2,3-DMN
Group D—1,2-DMN As a method for isolating 2,6-DMN from a mixture of isomers by means of crystallization, there is disclosed in Japanese Patent Publication No. 22553/1975, a method in which the mixture is cooled to −10 to 20° C. and the precipitated crystal is treated with methanol. The treatment with methanol is supposedly aimed at the improvement on the filterability of the crystal, but necessitates two-stage procedures. Japanese Patent Application Laid-Open No. 5767/1973 discloses a method in which a mixture of DMN isomers is washed or recrystallized by the use of an aromatic hydrocarbon. In this case, the mother liquor, which is formed after the separation of the crystal and contains the aromatic hydrocarbon, is usually isomerized to enhance the 2,6-DMN concentration and thereafter returned to the crystallization step. The aromatic hydrocarbon, when being contained in the isomerization procedure, which is usually carried out under a heating condition by using an acidic catalyst such as silica-alumina, zeolite and HF, causes partial disproportionation reaction to take place between DMN and the hydrocarbon, thus lowering the yield of the objective 2,6-DMN.

There is disclosed in the aforesaid Japanese Patent Publication No. 22553/1975 and Japanese Patent Application Laid-Open No. 5767/1973, that there is produced the objective 2,6-DMN having purity of 97.5 to 99.3%. However, any of the methods in the disclosures necessitates troublesome procedures and equipment therefor and requires a solid-liquid separation for the slurry obtained by crystallization in order to recover highly pure 2,6-DMN. In the case of industrial practice, the crystallization and solid-liquid separation need to be steadily carried out for a long period of time. Nevertheless, no description is so far found with regard to the change in the properties or purity of 2,6-DMN which is obtained in the case of continuously carrying out the crystallization and solid-liquid separation.

In addition, no detailed description is given of the means for separating the precipitated crystal from the mother liquor in any of the above-mentioned disclosures. In the case of separating the crystal from the slurry formed by crystallization for the sake of industrial practice, there are required simplified convenient equipment and procedures, stabilized running and a high separation efficiency. However, any description made from such industrial point of view is so far not found as to the means for isolating 2,6-DMN from the 2,6-DMN crystal-containing slurry obtained by crystallizing a mixture of DMN isomers.

SUMMARY OF THE INVENTION

The present inventors synthesized 1,5-DMN from o-xylene and butadiene as the starting raw materials and isomerized the resultant 1,5-DMN to obtain the mixture of isomers consisting essentially of 1,5-, 1,6- and 2,6-DMNs, which was cooled as it is to precipitate 2,6-DMN crystal in the form of scale. The crystal thus obtained was poor in the efficiency of separation from the mother liquor at the time of filtration, whereby it was difficult to obtain highly pure 2,6-DMN. As is the case with the foregoing, 2,6-DMN crystal in the form of scale was obtained from the mixture of isomers containing 2,7-, 1,7-DMN, etc. other than 1,5-, 1,6- and 2,6-DMN as the starting raw material for crystallization, but it was extremely poor in filtration efficiency.

It is judged from the above-mentioned phenomena that the method in which a mixture of DMN isomers is cooled as it is to precipitate 2,6-DMN in the form of crystal is not suited for industrial operation because of the inferior properties of the 2,6-DMN crystals to be precipitated.

It is the first object of the present invention to provide, under such circumstances, a process for isolating and recovering highly pure 2,6-DMN in an industrially advantageous manner by precipitating 2,6-DMN from a mixture of DMN isomers through crystallization to produce highly pure 2,6-DMN in high yield, wherein 2,6-DMN crystal having satisfactory filterability as well as favorable properties is made to precipitate.

A cooling-system tank-type crystallizer equipped with a stirrer and a jacket was continuously charged with the mixture of the isomers to precipitate 2,6-DMN crystal, while passing a coolant through the jacket. As a result, the precipitated crystal adhered closely to the inside wall of the crystallizer, whereby the heat transfer through the walls of the crystallizer was soon made insufficient, thus making it impossible to continue the procedure of precipitating the crystal. It is thought that the decrease in heat transfer performance has been caused by the crystal which precipitated on the heat transfer surface by locally lowered temperature of the slurry in the vicinity of the heat transfer surface as compared with the temperature of the other portion, and which adhered closely to the aforesaid surface.

As a method for preventing the trouble due to the adhesion of crystal to the heat transfer surface, there is disclosed in Japanese Patent Publication No. 25402/1986, a method in which the crystal precipitated on the heat transfer surface is scraped off. The disclosure insists that the heat transfer surface is always kept clean and the prescribed heat transfer performance is maintained, since the crystal precipitated on the heat transfer surface is physically removed. However, the above-mentioned method is accompanied with various troubles because of the sliding part installed inside the crystallizer which troubles are exemplified by frequent occurrence of sedimentation-solidification of the crystal in part in the crystallizer and of the abrasion or damage to scraping impellers that makes it impossible to continue crystal precipitaion procedures.

Specifically it is the second object of the present invention to provide a process for producing highly pure 2,6-DMN in an industrially advantageous manner by crystallizing 2,6-DMN to purify the same, wherein the trouble due to the aforesaid adhesion of the crystal is avoided to smoothly proceed with the procedure of precipitating the crystals.

In the case of the continuous crystallization procedure by the present inventors, the average retention time of the liquid to be crystallized in the crystallizer was 8 hours. As a result, separation of at least 99% pure crystal was possible during a short period after the start of the operation, but the purity of the crystal decreased with the lapse of time, thus making it impossible to maintain the prescribed purity of the crystal. The purity of the crystal as mentioned herein is the purity of the crystal to be fed to the next step of oxidation reaction, excluding a solvent and rinsing liquid that can easily be removed by distillation or the like.

It is the third object of the present invention to provide a process for steadily maintaining at least prescribed purity of 2,6-DMN for a long period of time in an industrially advantageous manner, in producing highly pure 2,6-DMN by precipitating 2,6-DMN through crystallization from a mixture of DMN isomers.

In the course of continuous separation of the crystal from the slurry containing the precipitated 2,6-DMN crystal in this continuous crystallization step, there was caused such trouble that filter cloths were plugged up in a short period of time, thereby lowering the filtering treatment capacity.

It is the fourth object of the present invention to provide under such circumstances, a process for steadily maintaining a prescribed filtering treatment capacity for a long period of time in an industrially advantageous manner in producing highly pure 2,6-DMN by precipitating 2,6-DMN through crystallization from a mixture of DMN isomers, followed by solid-liquid separation thereof.

In addition, it is the fifth object of the present invention to provide a process for producing 2,6-naphthalenedicarboxylic acid in an industrially advantageous manner preferably from o-xylene and butadiene as the starting raw materials based on the understanding of the above-mentioned process for producing 2,6-DMN.

Under such circumstances, intensive research and investigation were accumulated by the present inventors in order to attain the foregoing objects. As a result it has been found that highly pure 2,6-DMN can be produced from a mixture of DMN isomers in high yield in an industrially advantageous manner by putting the following processes into practice. The present invention has been accomplished on the basis of such finding and information.

With regard to the first object of the invention, that is, the process for improving the properties and filterability of the 2,6-DMN crystal precipitated by cooling a mixture of DMN isomers, it has been found that by making the crystallization system coexist with a solvent such as an aliphatic saturated hydrocarbon or an alicyclic saturated hydrocarbon, the properties of the precipitated crystal of 2,6-DMN change to a great extent and also the filterability thereof is markedly improved.

Specifically the present invention provides, in response to the first object and as the first aspect of the invention,
(1) a process for producing 2,6-DMN which comprises crystallizing 2,6-DMN from a mixture of DMN isomers in the presence of a solvent, preferably an aliphatic saturated hydrocarbon or an alicyclic saturated hydrocarbon.

With reference to the second object of the invention, that is, to avoid the trouble due to the adhesion of the crystal, it has been found that the procedure of precipitating the crystal can smoothly be effected by cooling the mixture of DMN isomers, while suppressing the adhesion of the crystal to the inside wall of the crystallizer by any of various effective means.

Specifically the present invention provides, in response to the second object of the invention,
(2) a process for producing 2,6-DMN which comprises crystallizing 2,6-DMN from a mixture of DMN isomers or a solution containing a mixture of DMN isomers by the use of a tank-type crystallizer, while suppressing the adhesion of the crystal to the inside wall of the crystallizer preferably by using for example, ① a method in which a crystallizer equipped with a heat transfer surface is used, a coolant is passed in contact with the heat transfer surface, the difference in temperature between the coolant and a mixture of DMN isomers or a solution containing a mixture of DMN isomers is maintained at 40° C. or lower; ② a method in which a solution containing a mixture of DMN isomers is concentrated by depressurizing the crystallizer or treating a solution containing a mixture of DMN isomers with an inert gas thereby evaporating a solvent in the solution containing a mixture of DMN isomers; or ③ a method in which a solution containing a mixture of DMN isomers is cooled by introducing a liquefied gas into the solution, thereby evaporating the gas.

In regard to the third object of the invention, on the basis of the understanding that the primary contributor to the decrease in the purity of the crystal during the continuous crystallization procedure is that the insufficiently grown crystal remaining in the crystallizer agglomerates with one another to form a macro agglomerate, while the mother liquor is incorporated inside the agglomerate, it has been found that the agglomeration of the crystal is suppressed, thereby enabling the long-term stable maintenance of at least prescribed purity of the crystal by taking countermeasure for accelerating the growth of the crystal itself or for suppressing the agglomeration of the crystal.

Specifically the present invention provides, in response to the third object of the invention,
(3) a process for producing 2,6-DMN which comprises crystallizing 2,6-DMN from a solution containing a mixture of DMN isomers by the use of a crystallizer, while suppressing the agglomeration of the crystal preferably by using for example, alone or in combination of at least two ① a method in which the average retention time of the crystal in the crystallizer is restricted to 6 hours at the longest; ② a method in which the agglomerate of the crystal is destroyed by circulating the slurry in the crystallizer by means of a circulation pump which is installed outside the crystallizer; or ③ a method in which the content in the crystallizer is stirred to the extent that the agglomeration of the crystal is suppressed.

The present invention further provides, in response to the third object thereof,
(4) a process for producing 2,6-DMN which comprises crystallizing 2,6-DMN from a solution containing a mixture of DMN isomers by the use of a crystallizer, while accelerating the growth of the crystal preferably by using, for example, ① a method in which the procedures of dissolving a part of the crystal and recrystallizing the dissolved crystal are carried out at least one time; or ② a method in which 2,6-DMN crystal which has been separately prepared is added as the seed crystal in the crystallizer.

With regard to the fourth object of the invention, on the basis of the understanding that the primary contributor to the filter cloth plugging up is that at the time of withdrawing the crystallization mother liquor, solvent or rinsing liquid by depressurization-suction, the solvent or rinsing liquid is evaporated to lower the temperature of the liquid on the filter cloth, whereby the crystal is precipitated at the stitches of the filter cloth, it has been found that stable filtering treatment capacity can be maintained by cleaning the filter cloth after filtration by using a solvent.

Specifically, the present invention provides, in response to the fourth object and as the second aspect of the invention, (5) a process for producing 2,6-DMN which comprises crystallizing 2,6-DMN from a mixture of DMN isomers in the presence of a solvent to precipitate the same, filtering the 2,6-DMN crystal thus precipitated by means of a filtering apparatus, separating the resultant filter cake from filter cloths, and thereafter cleaning the filter cloths by using a solvent.

Furthermore, the present invention provides in response to the fifth object and as the third aspect of the invention, (6) a process for producing a 2,6-naphthalenedicarboxylic acid which comprises subjecting the 2,6-DMN which is produced by the process as set forth in any of the preceding items (1) to (5) to liquid-phase oxidation; and
(7) a process as set forth in the preceding item (6), wherein the 2,6-DMN is produced by crystallizing the isomerization reaction product of 1,5-DMN which is formed from o-xylene and butadiene each as a starting raw material.

DESCRIPTION OF PREFERRED EMBODIMENT

The first aspect of the present invention relates to a process for producing 2,6-DMN by crystallizing 2,6-DMN from a mixture of DMN isomers in the presence of a solvent.

As the mixture of DMN isomers to be used as the starting raw material in the present invention, there are available a material separated from tar fraction or petroleum fraction, and a material produced by methylating naphthalene or methylnaphthalene, isomerizing the methylation product and isolating the resultant product. Particularly suitable materials are the isomerization reaction product of 1,5-DMN produced from o-xylene and butadiene as starting raw materials, the isomerization reaction product of the mother liquor which is formed by separating 2,6-DMN crystal from aforesaid isomerization reaction product of 1,5-DMN and the mixture of these isomerization reaction product.

In order to precipitate 2,6-DMN crystal in the process according to the present invention, the mixture of DMN isomers needs to have the following compositional ratio in view of the compositional ratio of the eutectic as mentioned hereinbefore.

1,5-DMN/2,6-DMN<1.9
2,7-DMN/2,6-DMN<1.4
2,3-DMN/2,6-DMN<1.1

Although depending on the catalyst to be used, the isomerization reaction product of 1,5-DMN synthesized from o-xylene and butadiene as starting raw material usually contains 5 to 20% of 1,5-DMN, 35 to 50% of 1,6-DMN, 35 to 50% of 2,6-DMN and at most 5% of the other DMN isomers, which satisfy the above-prescribed compositional ratio, and thus can be used for producing 2,6-DMN by cooling itself.

The mother liquor which is formed by separating 2,6-DMN crystal from the above-mentioned isomerization reaction product principally contains 1,5-DMN and 1,6-DMN and can be recycled as a raw material for isomerization. During isomerization reaction, however, side reaction is liable to take place, including the formation of methylnaphthalene (MMN) and trimethylnaphthalene (TMN) due to disproportionation and the formation of isomers belonging to 2,7-group due to the isomerization beyond 1,5-group. MMN and TMN can be removed by distillation, but the isomers outside 1,5-group are difficult to remove by distillation, and are accumulated in the system if the mother liquor is circulated through the isomerization step.

Detailed investigation was made by the present inventors on the relation between the concentration of the impurities in the raw material for crystallization and the concentration of impurities remaining in the objective crystal. As a result, there was observed a phenomenon that in the case where 2,7-DMN, MMN and/or TMN are present to a certain or more extent in the raw material for crystallization, 2,7-DMN, 2-MMN and/or part of TMN isomers remain in the objective crystal in amounts larger than the amount derived from eutetic theory, thereby making it difficult to obtain highly pure crystal.

As a result of further investigation, it has been found that the components such as 1,5-DMN, 1,6-DMN, 1-MMN and the isomer other than the above-remaining isomer in TMN that are contained in DMN isomerization reaction product to be used for raw material for crystallization can easily be removed by rinsing 2,6-DMN crystal after precipitation, and the concentration of such impurities steadily decreases with an increase in the amount of a rising liquid, but that 2,7-DMN, 2-MMN and part of TMN isomers hardly change in concentration even after rinsing the crystal and they are inevitably drawn and incorporated inside the crystal at the time of precipitation of 2,6-DMN as crystal instead of being attached, as the components of the mother liquor, onto the surface of the crystal.

The amounts of 2,7-DMN, 2-MMN and part of TMN isomers that are inevitably contained in the crystal at the time when the 2,6-DMN crystal is precipitated are determined approximately by the ratio by amount of each component to the dimethylnaphthalene series in the raw material for crystallization. When 10 parts by weight of 2,7-DMN is contained in 100 parts by weight of dimethylnaphthalene series, the amount of 2,7-DMN contained in 2,6-DMN crystal accompanied therewith is about 0.7 to 1.4% by weight. When 5 parts by weight of 2,7-DMN is contained in 100 parts by weight of dimethylnaphthalene series, the amount of 2,7-DMN contained in 2,6-DMN crystal accompanied therewith is about 0.4 to 0.8% by weight. On the other hand, when 5 parts by weight of MMN is contained in 100 parts by weight of dimethylnaphthalene series, the amount of 2-MMN contained in 2,6-DMN crystal accompanied therewith is about 0.7 to 1.3% by weight; and when 5 parts by weight of TMN is contained in 100 parts by weight of dimethylnaphthalene series, the amount of a part of TMN isomers contained in 2,6-DMN crystal accompanied therewith is about 0.2 to 0.6% by weight.

It is therefore desirable, in order to obtain 2,6-DMN having high purity of 98% or higher, that the concentration of 2,7-DMN based on dimethylnaphthalene series in the raw material for crystallization be set on at most 10% by weight when the raw material is almost free from MMN and TMN.

In the case where a considerable amount of MMN or TMN is contained in the raw material for crystallization, it is desirable, in order to restrict the concentrations of 2,7-DMN, MMN and TMN remaining in 2,6-DMN to at most 0.5% by weight, respectively, that the concentrations of 2,7-DMN, MMN and TMN based on dimethylnaphthalene series in the raw material for crystallization be set on at most 5%, 3% and 10% by weight, respectively.

The solvent to be used in the first aspect of the invention, which is in the form of liquid under working temperatures, is not specifically limited insofar as it is easily separated from DMN, but is preferably exemplified by aliphatic saturated hydrocarbons and alicyclic saturated hydrocarbons each having preferably 5 to 14, more preferably 6 to 12 carbon atoms. Specific examples thereof include pentane, hexane, heptane, octane, nonane, decane, undecane, dodecane, cyclopentane, cyclohexane, methyclopentane, methylcyclohexane, cyclooctane, methycyclooctane, decalin, methyldecalin and dimethyldecalin. The solvent may be used alone or in combination with at least one other.

The amount of the solvent to be used is determined taking into consideration the solubility of 2,6,DMN therein, 2,6-DMN concentration in the mixture of DMN isomers, operating temperature, slurry concentration and the like. Preferably the amount thereof is such that the crystallizing operation temperature is 10 to 60° C., especially around room temperature, and it is determined in the aforesaid manner. A crystallizing operation temperature lower than room temperature leads to the necessity for cooling energy, whereas that being unreasonably high leads to the necessity for heating energy.

The amount of precipitated crystal at the time of crystallization is preferably large because of higher crystal yield per unit operation. However, excessively large amount of crystal brings about difficulty in handling such as transportation and stirring. The slurry concentration is usually preferably 10 to 40% by weight. For example, when a mixture of DMN isomers containing 1,5-DMN, 1,6-DMN and 2,6-DMN in amounts of 8%, 46% and 46% by weight, respectively and n-heptane in one-half the amount of the mixture are mixed with heating to form a liquid and then cooled to 25° C., the slurry concentration becomes about 20% by weight.

In this way, the amount of the solvent to be used varies depending on a variety of factors, and is usually in the range of 0.01 to 20 times the weight of the mixture of DMN isomers. An amount thereof less than 0.01% by weight results in less effect on the improvement in the properties of 2,6-DMN crystal, thus forming crystal hard to filter; whereas that more than 20% by weight lowers economical efficiency, since the effect on the improvement in the crystal properties is not proportional to the amount used and the crystallizer becomes excessively large.

From the viewpoint of the balance between filterability and economical efficiency the amount thereof is preferably in the range of 0.1 to 10 times the weight of the mixture of DMN isomers.

The crystallizer to be used for precipitating 2,6-DMN crystal from the mixture of DMN isomers in the presence of a solvent is not specifically limited, but is available from those used for usual recrystallizing operation without any modification. A preferable crystallizer is a tank-type crystallizer. An apparatus for separating the crystal from the mother liquor after precipitating the crystal is not specifically limited as well, but is availble from those used for usual solid-liquid separation such as a centrifugal separator and a filter without any modification. The crystal is usually separated with a solid-liquid separator, and then rinsed preferably with the solvent same as that used in crystallization.

As mentioned hereinbefore, it is known that in purification by crystallization, the operability for filtration/separation and the purity of the objective crystal are greatly influenced by the properties of the crystal formed. Specifically, 2,6-DMN crystal precipitated from the mixture of DMN isomers, which is in the form of scale, has extremely poor filterability as mentioned hereinbefore. However, 1,5-DMN crystal precipitated therefrom, which is in the form of large plate, has excellent filterability. In this way, the crystal properties greatly change with change only in the position of a substituent group, and originate from the properties inherent in the substance itself forming the crystal.

By carrying out the crystallization in the presence of a solvent such as an aliphatic or alicyclic saturated hydrocarbon according to the invention, the properties of 2,6-DMN crystal are improved, thus facilitating industrial crystallizing separation. The properties of 2,6-DMN crystal can be improved by the use of an aromatic hydrocarbon as a solvent, but are improved to a greater extent by using an aliphatic or alicyclic saturated hydrocarbon. In order to enhance the yield of 2,6-DMN, there is adopted a system wherein the mother liquor formed by separating the crystal is usually employed for isomerization and the resultant isomerization liquid product is again crystallized. In this case, when an aromatic hydrocarbon as a solvent is used in the crysatllization, the mother liquor after the separation of the crystal contains the aromatic hydrocarbon. From the industrial standpoint, the aforesaid aromatic hydrocarbon is unsuitable as a coexistent material, since it is apt to bring about disproportionation reaction along with DMN in the isomerization step, thereby causing a fear of deteriorating the yield of the objective DMN.

2,6-DMN is somewhat soluble in any of the aforesaid hydrocarbons. Thus in order to obtain the same yield of 2,6-DMN crystal by using any of the hydrocarbons, the crystallization temperature needs to be lowered. The necessary lowering in the crystallization temperature varies depending upon the kind, use amount, etc. of the hydrocarbon. In the case of using a solvent of an aliphatic or alicyclic saturated hydrocarbon such as n-heptane in the same amount as the mixed liquid of DMN, the temperature at which 2,6-DMN begins to precipitate is about 25° C. lower than the temperature in a solventless case. It follows that lowering in the crystallization temperature increases the energy required for cooling, accordingly, the coexistence of an aliphatic or alicyclic saturated hydrocarbon is usually industrially unfavorable. At first glance, the coexistent substance in the process of the invention seems to be industrially unfavorable. Nevertheless the remarkable improvement in the properties of 2,6-DMN can exhibit a working effect which far outweighs the disadvantage.

The use of an aliphatic or alicyclic saturated hydrocarbon, in which DMN is less soluble than in an aromatic hydrocarbon is more advantageous than the use of an aromatic hydrocarbon, since it can mitigate the disadvantage of increased energy requirement as compared with the use of an aromatic hydrocarbon and since the use of the former decreases the viscosity of the crystallization mother liquor to a greater extent than the use of the latter.

The cause for the improvement in the properties of the precipitated 2,6-DMN crystal due to the coexistence of an aliphatic or alicyclic saturated hydrocarbon as a solvent is still unclear. It is known that a high crystal concentration in a slurry is apt to produce small crystal, but the aforesaid cause is not due to the effect on lowering the crystal concentration by the use of a solvent. Specifically, the crystal obtained by mixing an aliphatic or alicyclic saturated hydrocarbon with a mixture of DMN isomers, and then cooling the resultant mixture to precipitate 2,6-DMN crystal and form a slurry with a crystal concentration of 25% by weight, is favorable in properties and easy to filtrate as compared with the slurry obtained by cooling the mixture of DMN isomers alone to precipitate 2,6-DMN crystal and form a slurry with a crystal concentration of 25% by weight, which is hard to filtrate.

It is advantageous in the first aspect of the invention in response to the second object thereof at the time of crystallizing 2,6-DMN from a mixture of DMN isomers or a solution containing a mixture of DMN isomers through cooling or evaporation by the use of a tank-type crystallizer, to adopt for the puropose of suppressing the adhesion of the crystal to the inside wall of the crystallizer, any one of ① a method in which a crystallizer equipped with a heat transfer surface is used, a coolant is passed in contact with the heat transfer surface, the difference in temperature between the coolant and a mixture of DMN isomers or a solution containing a mixture of DMN isomers is maintained at 40° C. or lower; ② a method in which the solution containing DMN isomers is concentrated by depressurizing the crystallizer or treating a solution containing a mixture of DMN isomers with an inert gas, thereby evaporating a solvent in the solution containing the mixture of DMN isomer; or ③ a method in which a solution containing a mixture of DMN isomers is cooled by introducing a liquefied gas into the solution, thereby evaporating the gas.

At first, regarding the ① cooling method by indirect cooling by using a tank-type crystallizer equipped with a heat transfer surface, there are available a cooling method by using a jacketed tank-type crystallizer and passing a coolant through the jacket; a cooling method by installing a cooling coil inside a tank-type crystallizer and passing a coolant through the cooling coil; a cooling method by installing a heat exchanger outside a tank-type crystallizer and circulating the liquid to be crystallized through the heat exchanger with a pump or the like; and a cooling method in which the aforesaid methods are combined.

In such indirect cooling, the liquid to be crystallized is cooled from the wall surface through which heat is transferred, and if there is little difference in temperature between the liquid and a coolant, precipitation rate of the crystal is low, requiring a long retention time, whereas much temperature difference therebetween is liable to cause crystal adhesion onto the wall surface because of a high degree of supersaturation. The liability to adhesion onto the wall surface depends upon the properties inherent to the crystal in question, the kind of the crystal and the precipitation conditions at the time of crystal precipitation.

As a result of experimental investigation made by the present inventors on a method capable of controlling the degree of supersaturation, preventing the adhesion of the precipitated crystal onto the wall surface and precipitating the crystal at a practically sufficient rate, it has been found that in the case of precipitating 2,6-DMN crystal by cooling a mixture of DMN isomers, the adhesion of the crystal onto the wall surface is almost negligible provided that the difference in temperature between the liquid to be crystallized and the coolant is maintained at 40° C. or lower, and even if the adhesion is not negligible, it does not cause difficulty in continuing the crystallizing operation.

In carrying out the crystallizing operation, when the above-mentioned difference in temperature is kept at 40° C. or lower, the crystal adhesion thereonto is almost negligible even if the mixture of DMN isomers is cooled as it is. However, 2,6-DMN crystallized under a solventless condition has unfavorable crystal properties due to its scaly state and is hard to filter, whereby highly pure 2,6-DMN is made difficult to obtain after filtration separation.

The use of a hydrocarbon as a solvent, especially an aliphatic or alicyclic saturated hydrocarbon in precipitating the crystal improves the crystal properties, thus enabling highly pure 2,6-DMN to be formed after filtration separation.

For the purpose of preventing the crystal from adhering onto the wall surface, a solvent is not always necessary, but in order to obtain highly pure 2,6-DMN crystal it is indispensable to employ a solvent.

In the case of crystallizing 2,6-DMN by using a solvent, the above-mentioned method ② is usable in place of the method 1 to evaporate the solvent and utilize the latent heat of evaporation to effect concentration. The methods for evaporating the solvent include a method of depressuring the crystallizer inside, a method of feeding an inert gas and the like methods. In the case of concentration by evaporating the solvent, the crystal is formed inside the crystallizer not on the inner wall thereof, whereby the adhesion onto the inner wall is less apt to take place.

The method ③ in which a liquefied gas such as liquefied butane or propane is blown into the raw material to be crystallized and effect cooling by utilizing the latent heat of evaporation can exhibit the same effect as the solvent evaporation.

The amount of the solvent to be used varies depending upon various factors. In the case of indirect cooling for crystallization according to the method ①, by the reason same as that described hereinbefore, the amount is 0.01 to 20 times, preferably 0.1 to 10 times the weight of the mixture of DMN isomers.

In the case of concentration by evaporating the solvent according to the method ②, since the amount of the solvent in the crystallizer varies as the solvent evaporates, the solvent is supplied at need during the crystallizing operation so that the amount of the solvent after evaporation falls within the above-prescribed range. The inert gas to be used for treating and evaporating the solvent is exemplified by nitrogen, argon and carbon dioxide gas.

In the case of cooling by evaporating the liquefied gas according to the method ③, the operating temperature and pressure are selected according to the liquefied gas to used, and the liquefied gas is supplied in the crystallizer so that the slurry concentration at the time of crystallization falls within the above-prescribed range.

It is also advantageous in the first aspect of the invention in response to the third object thereof, at the time of crystallizing 2,6-DMN from a solution containing a mixture of DMN isomers through cooling or evaporation by the use of a tank-type crystallizer, to adopt, for the purpose of suppressing the agglomeration of the crystal, one or at least two in combination of ① a method in which the average retention time of the crystal in the crystallizer is restricted to 6 hours at the longest; ② a method in which the agglomerate of the crystal is destroyed by circulating the slurry in the crystallizer by means of a circulation pump which is installed outside the crystallizer; and ③ a method in which the content in the crystallizer is stirred to the extent that the agglomeration of the crystal is suppressed.

In crystallizing separation, attention is usually paid to the formation of large crystal. The reason for this is that larger crystal leads to a decrease in surface area per unit weight of the crystal, resulting in enhanced purity due to a decrease in the amount of the accompanying mother liquor and at the same time, facilitates solid-liquid separation.

The operations in the aforestated methods ① to ③ in the present invention are all to be avoided in order to enlarge crystal, and are fundamentally contrary to and different from the prevailing methods according to the prior arts.

In general, an increase in retention time in a crystallizer causes growth and enlargement of crystal. By utilizing this property of the crystal there is often adopted a method in which the retention time is prolonged by installing an aging tank separately from the crystallizer. However, as a result of investigation made by the present inventors on the crystallization of 2,6-DMN from a mixture of DMN isomers, it has been found that an increase in the retention time is apt to cause agglomeration of crystal rather than crystal growth and that the agglomeration is suppressed and highly pure 2,6-DMN crystal can steadily be collected over a long time by restricting the average retention time on the basis of the further investigation on the relationship between the average retention time and a change in crystal purity.

In the case of preventing the crystal agglomeration by restricting the retention time in a crystallizer according to the present invention, the average retention time is usually at most 6 hours, preferably at most 4 hours, more preferably at most 3 hours. A decrease in the retention time increases the proportion of non-agglomerated crystal in the form of plate and suppresses the agglomeration in the direction of thickness, whereby the crystal is made thin as a whole though the equivalent diameter thereof remains almost unchanged. Consequently, the purity of the crystal is enhanced and highly pure 2,6-DMN crystal is steadily obtained according to the above-prescribed retention time.

Moreover, it has been found by the present inventors that the agglomerate of 2,6-DMN crystal is comparativley easily destroyed by applying a shearing force thereto but individual crystal is not easily destroyed thereby. In principle, application of a shearing force in crystallization is said to be avoided, since such a shearing force crushes the crystal to miniaturize the same. However, so far as the 2,6-DMN crystal is concerned, by applying a shearing force, the agglomeration of the crystal is suppressed, the amount of the mother liquor accompanying the crystal is decreased with comparatively less crushing of the crystal, and consequently excellent effect is exhibited on enhancing the purity of the crystal cake. Such property inherent in the 2,6-DMN crystal has never been reported to date.

The method for applying a shearing force is exemplified for example, by a method in which the slurry in the crystallizer is circulated by means of a circulation pump installed therein and the shearing force can be controlled by regulating and selecting the circulation rate and suitable type of the pump. The circulation rate suitable for suppressing and disintegrating the agglomerate varies depending upon the type of the tank-type crystallizer, and the ratio of the slurry circulation rate in the crystallizer to the feed rate of the raw material is preferably at least 1.0.

The disintegration means by shearing force, when provided in the crystallizer, can suppress the agglomeration in the direction of length thus decreasing the equivalent diameter of the agglomerate, though the proportion of the agglomerate based on the whole slurry and the thickness thereof do no appreciably change. Consequently, the purity of the crystal is enhanced and highly pure 2,6-DMN crystal is continuously obtained.

Another means for preventing the agglomeration is intensification of agitation in the crystallizer. Such intensification usually leads to the miniaturization of the crystal, and thus it is a general and customary practice to restrict the agitation strength to the extent that necessary circulating stream is maintained. Specifically, application of excessive agitation strength is said to be avoided in crystallization. Nevertheless as far as the 2,6-DMN crystal is concerned, it was observed that by intensifying the agitation in the crystallizer, the agglomeration of the crystal is suppressed, the amount of the mother liquor accompanying the crystal is decreased with comparatively less crushing of the crystal, and consequently excellent effect is exhibited on enhancing the purity of the crystal cake. This property, which is similar to that relating to the aforesaid shearing force, has never been reported to date.

The agitation strength for suppressing the agglomeration of 2,6-DMN crystal varies depending upon the form of the crystallizer and the like, and the power value (PV) per unit volume of the crystallizer is preferably at least $1.0 \text{ kW/m}^3$, approximately. Intensification of the agitation can suppress the agglomeration in the direction of length, thus decreasing the equivalent diameter of the agglomerate though the proportion of the agglomerate based on the whole slurry and the thickness thereof do not appreciably change. Consequently, the purity of the crystal is enhanced and highly pure 2,6-DMN crystal is continuously obtained. The slurry crystallized by any of the methods which suppress the agglomeration of the crystal can decrease the amount of the mother liquor accompanying the crystal.

Mention has been made of the three means as described above. Any other means capable of suppressing the agglomeration of the crystal is effective for enhancing the purity of the crystal cake. Any of the three means may be used alone or in combination with at least one other.

The crystallizer for carrying out the present invention is not specifically limited, but is selected according to each of the methods. Likewise, an apparatus for separating the crystal from the mother liquor after precipitating the crystal is not specifically limited, but may be selected for use without modification from the apparatus usually used for solid-liquid separation such as a centrifugal separator and a filter. The crystal is usually separated in a solid-liquid separator and then rinsed to afford highly pure 2,6-DMN.

In the case where further highly pure 2,6-DMN is required, such 2,6-DMN is obtained, as is described hereinafter in the working examples, by dispersing again the 2,6-DMN crystal obtained by any of the foregoing methods in a solvent and thereafter separating the crystal.

It is also advantageous in the first aspect of the invention in response to the third object thereof, at the time of crystallizing 2,6-DMN from a solution containing a mixture of DMN isomers through cooling or evaporation by the use of a tank-type crystallizer, to adopt, for the purpose of accelerating the growth of the crystal, any one of ① a method in which the procedures of dissolving a part of the crystal, and recrystallizing the dissolved crystal are carried out at least one time; and ② a method in which 2,6-DMN crystal which has been separately prepared is added as the seed crystal in the crystallizer.

As a method for accelerating the growth of the crystal, consideration is given to a method in which excessive nucleus generation is suppressed by decreasing the degree of supersaturation in the crystallizer. The method, however involves the problem that the yield of the crystal per unit time per unit volume of crystallizer is decreased, thereby lowering the productivity.

Liability to agglomerzation or growth of crystal is the property inherent in the crystal in question and varies depending upon each substance. It has been found by the present inventors that the 2,6-DMN crystal is liable to agglomeration and the agglomeration is suppressed by accelerating crystal growth. Based on and in response to such properties, a new method for crystallization has been developed.

In the case of heating the slurry in the crystallizer to dissolve a part of the crystal and then recrystallizing the dissolved crystal according to the method ①, the agglomerate is decreased and large crystal is obtained, presumably because a part of the crystal is dissolved by heating and simultaneously the agglomerate is disintegrated, and at the time of subsequent cooling, 2,6-DMN crystal is precipitated on the surfaces of the crystal released from the agglomerate, thereby accelerating crystal growth.

In this way, the 2,6-DMN crystal is grown without being accompanied with the mother liquor by repeating the procedure of dissolution and recrystallization by heating and cooling. When the liquid to be crystallized is subjected to this heat history at least once from the feeding of the raw material in the crystallizer to the withdrawal therefrom into the solid-liquid separation step, the whole crystal in the crystallizer is sufficiently grown, resulting in remarkable enhancement of crystal purity.

In addition, according to the method ②, large crystal is obtained by adding in the crystallizer, 2,6-DMN crystal which has been separately prepared as the seed crystal. In order to obtain large crystal, the retention time is prolonged in conventional method. Nevertheless 2,6-DMN crystal, when left in the crystallizer for a long time, is liable to agglomeration rather than the crystal growth, thereby making it impossible to collect highly pure crystal.

The seed crystal, when fed in the crystallizer, can suppress the agglomeration and cause the crystal to sufficiently grow even for a long retention time. For the purpose of enhancing the productivity, shorter retention time is desirable. In this case, crystallization is carried out at a considerably high degree of supersaturation. Unless the seed crystal is fed, a large amount of nuclei is generated, thus preventing sufficient growth of the crystal. On the other hand, the seed crystal, when being present at a proper concentration, contributes to sufficient growth of the crystal by precipitating 2,6-DMN on the surfaces of the seed crystal and also to marked enhancement of the purity of the objective crystal. This is presumably because precipitation of the crystal on the surfaces of the seed crystal prevails over crystal agglomeration.

The method for preparing the seed crystal to be used in the method ② is not specifically limited provided that it is grown to some extent. For example, the seed crystal can be formed by feeding the raw material for crystallization in a seed crystal preparation tank and crystallizing the same by a batchwise process at a sufficiently low cooling rate of the liquid to be crystallized or at a sufficiently low distillation rate of the solvent. Alternatively, the seed crystal can be formed by carrying out at least one time, the steps of taking out a part of the slurry in the crystallizer, feeding the same in the seed crystal preparation tank, once dissolving a part of the crystal by raising the temperature thereof, adding a solvent or the like procedure, and then recrystallizing the slurry by cooling or removing the solvent. The seed crystal formed by the latter method is particularly suitable for the purpose.

Any method other than the foregoing can enhance the crystal purity, provided that the method is capable of accelerating crystal growth.

The second aspect of the invention relates to a process for producing 2,6-DMN which comprises crystallizing 2,6-DMN from a mixture of DMN isomers in the presence of a solvent to precipitate the same, filtering the 2,6-DMN crystal thus precipitated by means of a filtering apparatus, separating the resultant filter cake from filter cloths, and thereafter cleaning the filter cloths by using any of various solvents, preferably at a temperature not lower than a filtering temperature.

It is preferable in the second aspect of the invention that the slurry obtained by crystallization be continuously filtered by the use of a rotary vacuum filter (hereinafter abbreviated to "RVF"). RVF is a continuous solid-liquid separation apparatus in which a part of a cylindrical filter cloth is immersed in a slurry to filter the slurry with suction by rotating the filter cloth. In a RVF, the cake which is formed on the filter cloth by immersing the filter cloth in the slurry and depressuring the cylinder inside to suck mother liquor, is washed with a suitable rinsing liquid and is peeled off from the filter cloth for recovery thereof. The recovered cake contains a solvent and the rinsing liquid, but can be made into highly pure 2,6-DMN by removing the solvent and the rinsing liquid by means of distillation or the like method.

A RVF is imparted with excellent advantages in that the use thereof enables not only solid-liquid separation but also a series of continuous operations including cake rinsing, suction of the rising liquid and cake peeling off and further enables highly pure 2,6-DMN to be produced by continuous single-stage operation. A RVF is advantageous in that mechanical troubles are less apt to occur because of a low rotational speed and that the maintenance work is simplified.

In the case of solid-liquid separation by means of a RVF, the steps of immersing a filter cloth in slurry, sucking mother liquor, rinsing cake and peeling the cake are carried out in turn. The mother liquor remaining in the cake is sucked and then the cake collected on the filter cloth which has been immersed in the slurry is washed with a proper rinsing liquid. Preferably, the rinsing liquid is the same as the solvent which is used in the crystallization. Subsequently the rinsing liquid remaining in the cake is sucked, and the cake is peeled off from the filter cloth and recovered. The solvent and rinsing liquid still remaining in the cake are removed from the cake thus recovered to afford highly pure 2,6-DMN.

In the second aspect of the invention, the filter cloth is washed from the time of the cake peeling to the time of the filter cloth immersion in the slurry. This washing enables 2,6-DMN which is the cause for filter cloth plugging up to be dissloved and the filtering treatment capacity to be steadily maintained for a log period of time without discontinuing the RVF operation. The operation of washing the filter cloth may be carried out continuously at all times or intermittently according to the degree of filter cloth plugging up.

The cleaning liquid for the filter cloth to be used in the second aspect of the invention is to be liquid under the operational conditions, capable of dissolving 2,6-DMN and compatible with the mother liquor and the rinsing liquid and preferably be low in reactivity with 2,6-DMN and easily separable from DMN. The cleaning liquid is not specifically limited, but is preferably the same as the solvent for crystallization or the cake rinsing liquid from the viewpoint of recovery and separation of the mother liquor, the rinsing liquid and the cleaning liquid.

The above-mentioned aliphatic and alicyclic saturated hydrocarbons suitable for crystallization are imparted with all the necessary requirements, that is, being in the form of liquid, capability of dissolving 2,6-DMN, compatibility with the mother liquor and the rinsing liquid, low reactivity with 2,6-DMN and easiness of separation from DMN, and thus are preferably usable as the cleaning liquid for the filter cloth.

The cleaning of the filter cloth is intended for dissolving on the filter cloth, the crystal precipitated by cooling, and is conducted preferably at a temperature not lower than the filtration temperature, that is, the slurry temperature. The use of a hot solvent as the cleaning liquid for the filter cloth enables high performance cleaning effect, thus minimizing the period of time required for the cleaning as well as the amount of the cleaning liquid to be used.

The amount of the cleaning liquid per unit time for achieving satisfactory cleaning effect is determined by the filter cloth area and the filter constitution. In the case of using a hot solvent which enables high performance cleaning effect, the amount of the cleaning liquid to be used can be decreased by intermittently carrying out the cleaning at a regular time interval. The aforesaid amount per unit time and cleaning hours are determined so as to select optimum conditions taking the expectable cleaning effect into consideration.

As described hereinbefore, it is well suited for the production of 2,6-DMN crystal to carry out filtration by the use of a filter such as a RVF, to use a solvent capable of dissolving the crystal as the cleaning liquid for filter cloth at the time of cleaning the filter after peeling off the cake, and to set the cleaning temperature on a temperature not lower than the filtration temperature, that is, the slurry temperature. The aforesaid procedures are applicable not only to the 2,6-DMN crystal system but also to the recovery of crystal from a slurry in general.

In this way, it is made possible according to the first and second aspects of the present invention to continuously operate the filter (RVF,etc.) and produce highly pure 2,6-DMN steadily for a long period of time without causing filter cloth plugging up by cleaning the filter cloth after filtration to clean the crystal stuck to the filter cloth, to minimize filter cloth cleaning hours and the consumption of the cleaning liquid by cleaning the filter cloth at a high temperature, and thus to proceed with the curtailment of utilities required, and labor saving in the operation, thereby realizing the industrially advantageous production of highly pure 2,6-DMN.

Moreover the third aspect of the invention relates to a process for producing a 2,6-naphthalenedicarboxylic acid by subjecting the 2,6-DMN produced according to the first and second aspects of the invention to liquid-phase oxidation.

Particulary preferable 2,6-DMN to be used in the third aspect of the invention includes 2,6-DMN which is obtained by isomerizing 1,5-DMN produced from o-xylene and butadiene as starting raw materials, and subjecting the resultant isomerization reaction product to a crystallizing treatment according to the first aspect of the invention; 2,6-DMN which is obtained by filtering treatment according to the second aspect of the invention; and 2,6-DMN which is obtained according to the combination of the first and second aspects of the invention. The isomerization reaction product from 1,5-DMN is produced by cyclizing o-tolylpentene-2 formed from o-xylene and butadiene to produce 1,5-demethyltetralin, dehydrogenating the same to produce 1,5-DMN and isomerizing the 1,5-DMN, and is a mixture of isomers consisting essentially of 1,5-, 1,6- and 2,6-DMN.

The liquid-phase oxidation process for 2,6-DMN can be selected for use from the conventional well-known process without specific limitation. In general, mention may be made of a process in which 2,6-DMN is subjected to liquid-phase oxidation by molecular oxygen in a solvent such as acetic acid in the presence of a catalyst of Co—Mn—Br system, and more specifically, of a process in which 2,6-DMN is subjected to liquid-phase oxidation by air in a solvent comprising acetic acid or water-containing acetic acid containing a small amount of water in the presence of a catalyst composed of a cobalt compound, a manganese compound and a bromine compound under reactional conditions including a pressure of 5 to 40 Kg/cm$^2$G, approximately and a temperature of 180 to 250° C., approximately, which process enables the production of 2,6-naphthalenedicarboxylic acid at a high yield of 80% or more. The catalyst is used in amounts of usually 0.002 to 0.1 mol as cobalt atom, 0.01 to 0.2 mol as manganese atom and 0.01 to 0.2 mol as bromine atom each based on one mol of 2,6-DMN as the starting raw material.

According to the process of the present invention for producing 2,6-DMN, the precipitated 2,6-DMN crystal is remarkably improved in filterability with great change in its properties, and highly pure 2,6-DMN is obtained in high yield in an industrially advantageous manner by making an aliphatic or alicyclic saturated hydrocarbon as a solvent coexist in the crystallizing treatment of the mixture of DMN isomers. It is particularly effective to use, as the mixture of DMN isomers, the isomerization reaction product from 1,5-DMN which is formed from o-xylene and butadiene as the starting raw materials.

By subjecting the 2,6-DMN thus obtained to liquid-phase oxidation, a 2,6-naphthalenedicarboxylic acid is extremely advantageously produced which is useful as a starting raw material for high performance polyester, and the like. In addition, by esterifying the 2,6-naphthalenedicarboxylic acid thus obtained, a corresponding ester, for example, a methyl ester is efficiently obtained.

In the following, the present invention will be described in more detail with reference to working examples, which however shall not limit the present invention thereto. The concentration of each of the components in the following working examples, comparative examples and reference examples was obtained by gas chromatography.

REFERENCE EXAMPLE 1

DMN comprising as a principal component, 1,5-DMN which had been synthesized from o-xylene and butadiene as starting raw materials was isomerized in the presence of HF as the catalyst to afford a DMN isomerization reaction product having chemical composition as given in Table 1.

REFERENCE EXAMPLE 2

DMN comprising as a principal component, 1,5-DMN which had been synthesized from o-xylene and butadiene as starting raw materials was isomerized in the presence of mordenite (produced by Tosoh Corporation) as the catalyst to afford a DMN isomerization reaction product having chemical composition as given in Table 1

TABLE 1

| Composition (wt %) | Reference Example 1 | Reference Example 2 |
| --- | --- | --- |
| 1,5-DMN | 8.54 | 15.73 |
| 1,6-DMN | 41.12 | 45.87 |
| 2,6-DMN | 48.73 | 35.10 |
| Other DMN isomers | 0.14 | 0.39 |
| Low boiling substances | 0.60 | 1.80 |
| High boiling substances | 0.87 | 1.11 |

[First aspect of the invention]

EXAMPLE 1

100 g of the DMN isomerization reaction product produced in Reference Example 1 and 100 g of n-heptane were placed in a 400 milliliter (mL) glass container equipped with a stirrer under stirring and heating to 75° C. to form homogeneous liquid as a whole. It was cooled under stirring to 50° C., then further cooled to 20° C. over a period of 2 hours, and maintained thereat for 30 min. to precipitate crystal. The precipitated crystal was in the form of board. The content in the glass container was filtered by suction with a G2 glass filter (standard maximum diameter of opening of 100 to 150 μm), and the crystal thus obtained was analyzed. As a result, the purity of the 2,6-DMN crystal was 91.3%. After the filtration by suction, the crystal was rinsed with 30 g of n-heptane at 20° C. to afford 32.6 g of DMN crystal having chemical composition as given in Table 2. The percentage of 2,6-DMN in the resultant crystal based on 2,6-DMN in the starting raw material (hereinafter referred to as "crystal yield") was 66.4%.

EXAMPLE 2

The procedure in Example 1 was repeated to precipitate crystal except that 60 g of cyclohexane was used in place of 100 g of n-heptane. The precipitated crystal was in the form of board. The content in the glass container was filtered by suction with a G2 glass filter, and the crystal thus obtained was analyzed. As a result, the purity of the 2,6-DMN crystal was 88.7%. After the filtration by suction, the crystal was rinsed with 30 g of n-heptane at 20° C. to afford 34.0 g of DMN crystal having chemical composition as given in Table 2 at a crystal yield of 69.1%.

Comparative Example 1

The procedure in Example 1 was repeated to precipitate crystal except that the DMN isomerization reaction product was used in an amount of 200 g and that the use of n-heptane was intentionally omitted. The precipitated crystal was in the form fine scale. The content in the glass container was filtered by suction with G2 glass filter and the crystal thus obtained was analyzed. As a result, the purity of the 2,6-DMN crystal was 74.1%. After the filtration by suction, the crystal was rinsed with 100 g of n-heptane at 20° C. to afford 88.2 g of DMN crystal having 2,6-DMN purity of 83.0% at a crystal yield of 75.1%.

Comparative Example 2

200 g of the DMN isomerization reaction product produced in Reference Example 1 was placed in a 400 milliliter (mL) glass container which had been used in Example 1 under heating to 75° C. to melt into liquid as a whole. It was cooled to 45° C. over a period of 2 hours, and maintained thereat for 30 min. to precipitate crystal. The precipitated crystal was in the form of fine scale. The content in the glass container was filtered by suction with a G2 glass filter and the crystal thus obtained was analyzed. As a result, the purity of the 2,6-DMN crystal was 78.2%. After the filtration by suction, the crystal was rinsed with 100 g of n-heptane at 20° C. to afford 74.6 g of DMN crystal having 2,6-DMN purity of 84.7% at a crystal yield of 64.8%. Although the crystal yield is comparable to that in Example 1, 2,6-DMN purity is remarkable low as compared with that in Example 1 in spite of the amount of n-heptane used for rinsing much larger than the amount in Example 1.

EXAMPLE 3

The procedure in Example 1 was repeated to carry out crystallization, filtration and rising except that toluene was used in place of n-heptane. As a result, there was obtained 29.6 g of DMN crystal having chemical composition as given in Table 2 at a crystal yield of 57.4%. The precipitated crystal was larger than that obtained by cooling the DMN isomerization reaction product as such under a solventless condition, but was smaller than that obtained by using n-heptane. The purity of the resultant crystal was higher than that obtained by cooling the DMN isomerization reaction product as such under the solventless condition, but was lower than that obtained by using n-heptane.

EXAMPLE 4

The procedure in Example 1 was repeated to precipitate crystal except that 100 g of the DMN isomerization reaction product produced in Reference Example 2 and 100 g of isooctane were used in place of the product from Reference Example 1 and n-heptane, and that the homogeneous liquid was cooled from 50° C. to 0° C. over a period of 3 hours. The precipitated crystal was in the form of board. Then the content in the glass container was filtered by suction with a G2 glass filter, and the crystal thus obtained was analysed. As a result, the purity of the 2,6-DMN was 86.3%. Thereafter, the crystal was rinsed with 30 g of isooctane at 0° C. to afford 24.8 g of DMN crystal having chemical composition as given in Table 2 at a crystal yield of 70.1%.

TABLE 2

| Composition (wt %) | Example 1 | Example 2 | Example 3 | Example 4 |
| --- | --- | --- | --- | --- |
| 1,5-DMN | 0.12 | 0.15 | 0.91 | 0.21 |
| 1,6-DMN | 0.56 | 0.73 | 4.39 | 0.61 |
| 2,6-DMN | 99.31 | 99.10 | 94.54 | 99.15 |
| Other DMN isomers | <0.01 | <0.01 | <0.01 | <0.01 |
| Low boiling substances | <0.01 | 0.01 | 0.06 | 0.02 |
| High boiling substances | 0.01 | 0.01 | 0.09 | 0.01 |

Comparative Example 3

200 g of the DMN isomerization reaction product produced in Reference Example 2 was placed in a 400 milliliter (mL) glass container which had been used in Example 1 under heating to 75° C. to melt into liquid as a whole. It was cooled to 45° C. over a period of 2 hours, and maintained thereat for 30 min. to precipitate crystal. The precipitated crystal was in the form of fine scale. The content in the glass container was filtered by suction with a G2 glass filter and the crystal thus obtained was analyzed. As a result, the purity of the 2,6-DMN crystal was 68.5%. After the filtration by suction, the crystal was rinsed with 100 g of n-heptane at 20° C. to afford 30.5 g of DMN crystal having 2,6-DMN purity of 77.3% at a crystal yield of 33.6%. Although the crystal concentration at the time of crystallization was almost the same as that in Example 4, 2,6-DMN purity is remarkably low because of the poor properties of the precipitated crystal in spite of the amount of the rinsing liquid much larger than the amount in Example 4.

EXAMPLE 5

A mixture of DMN isomers comprising 1,5-DMN as a principal component and a mixture of DMN isomers comprising 1,7-DMN as a principal component were mixed and isomerized in the presence of mordenite type H as the catalyst to afford a DMN isomerization reaction product (starting raw material for crystallization) having chemical composition as given in Table 3.

100 g of the DMN isomerization reaction product produced in such a manner and 100 g of n-heptane ware placed in a 400 milliliter (mL) glass container equipped with a stirrer under stirring and heating to 75° C. to form homogenerous liquid as a whole. It was cooled under stirring to 50° C., then further cooled to 10° C. over a period of 3 hours, and maintained thereat for 30 min. to precipitate crystal. The precipitated crystal was in the form of board. The content in the glass container was filtered by suction with a G2 glass filter, and the crystal thus obtained was analyzed. As a result, the purity of the 2,6-DMN crystal was 90.7%. After the filtration by suction, the crystal was rinsed with 30 g of n-heptane at 10° C. to afford 24.1 g of DMN crystal having chemical composition as given in the Table 3 at a crystal yield of 60.6%.

EXAMPLE 6

The procedure in Example 5 was repeated to carry out crystallization, filtration and rinsing except that decalin was used in place of n-heptane. As a result, there was obtained DMN-crystal having chemical composition as given in Table 3 in an amount of 23.6 g at a crystal yield of 59.4%.

TABLE 3

| Composition (wt %) | Starting raw material for crystallization | Example 5 | Example 6 |
| --- | --- | --- | --- |
| 1,5-DMN | 11.12 | 0.11 | 0.10 |
| 1,6-DMN | 35.09 | 0.36 | 0.31 |
| 2,6-DMN | 39.44 | 99.13 | 99.25 |
| 1,7-DMN | 5.43 | 0.03 | 0.04 |
| 2,7-DMN | 4.71 | 0.31 | 0.25 |
| Other DMN isomers | 2.03 | 0.03 | 0.02 |
| Low boiling substances | 1.36 | 0.02 | 0.02 |
| High boiling substances | 0.82 | 0.01 | 0.01 |

[First aspect of the invention: suppression of crystal adhesion]

EXAMPLE 7

Crystallizing operation was carried out by the use of a tank-type crystallizer comprising a vertical cylindrical vessel which had an inside diameter of 1000 mm and a cylinder length of 2000 mm and was equipped with a stirrer; a cooling jacket with a heat transfer area of 5.1 $m^2$; 4 baffle plates inside; a thermometer inserted at the bottom portion thereof for measuring the temperature of the content in the vessel; and an overflow pipe at the top portion thereof for maintaining the volume of the liquid (slurry) in the vessel at 1.3 $m^3$ by withdrawing the content therethrough as an overflow.

The mixture of 1,5-DMN and n-heptane as the solvent was isomerized to afford an isomerization reaction product having chemical composition as given in Table 4. This product as the starting raw material for crystallization was heated to 80° C. to form homogeneous liquid as a whole, preliminarily fed in the crystallizer at 80° C. up to the overflow level and cooled with stirring to 60° C. When the temperature inside the crystallizer reached 60° C., the raw material at 80° C. was continuously fed therein from the bottom at a constant rate of 200 kg/hr, which was the starting time of crystallizing operation.

Simultaneously with the starting time, cooling water at 40° C. was passed through the jacket to cool the content in the crystallizer, the temperature of which was maintained at 80°0 C. by regulating the flow rate of the cooling water at 40° C. to be passed through the jacket. The content there in was mixed at an agitation power of 1.8 kW/$m^3$, and the slurry containing precipitated crystal was continuously taken out from the top portion as the overflow. The aforesaid operation was continued for 24 hours, during which time the cooling performance of the jacket and the cooling water flow rate of 0.17 $m^3$/hr in average were stabilized, enabling continuous operation without any trouble. The concentration of the crystal in the slurry which was continuously taken out by overflowing was also stable at about 14% by weight.

After the lapse of 24 hours, the feeding of the raw material and the cooling water was stopped, and the slurry and cooling water were entirely withdrawn through the bottom of the crystallizer. Then, the inside of the vessel was observed. As a result, no crystal adhesion was observed even at the jacket fitted portion. The crystal was separated from the resultant slurry and recovered as 2,6-DMN having purity of 99.2%.

The above-mentioned procedure was repeated except that the cooling water temperature was set at 10° C. The flow rate of the cooling water was 0.07 $m^3$/hr at the start of the crystallizing operation and was comparatively stable until 3 hours after the start. However, after the lapse of 3 hours from the start thereof, the flow rate of the cooling water began to increase because of lowered heat transfer performance, and after the lapse of 8 hours therefrom, the flow rate reached its upper limit of 5.0 $m^3$/hr. Thereafter the temperature inside the crystallizer began to rise because of the insufficient cooling capacity. Thus after the lapse of 8.5 hours therefrom, feeding of the raw material and the cooling water was stopped. Then the slurry and cooling water were entirely withdrawn through the bottom of the crystallizer, and the inside of the vessel was observed. As a result, there was observed crystal scale in a thickness of about 5 mm stuck to the jacket fitted portion.

EXAMPLE 8

Crystallizing operation was carried out by the use of a tank-type crystallizer comprising a vertical cylindrical vessel which had an inside diameter of 1000 mm and a cylinder length of 3000 mm and was equipped with an overhead condenser; a gas-liquid separator at the top portion; 4 baffle plates inside; and a thermometer inserted at the bottom portion thereof for measuring the temperature of the content in the vessel, so that the components evaporated in the vessel were condensed in the condenser and separated in the separator into liquid components to be circulated through the vessel and gaseous components to be sucked with a vacuum pump.

The isomerization reaction liquid product from 1,5-DMN and n-heptane as the solvent were mixed to afford a mixture of DMN and n-heptane having chemical composition as given in Table 4. This mixture as the starting raw material for crystallization was heated to 65° C. to form homogeneous liquid as a whole.

Firstly, the crystallizer was charged with 1.3 $m^3$ of n-heptane at about 40° C. and was gradually depressurized. When the pressure in the crystallizer reached 90 Torr. the n-heptane began to boil, and simultaneously therewith the feeding of the raw material kept at 65° C. was started at a feed rate of 200 kg/hour, which was kept constant during the crystallizing operation. The raw material was fed at a middle stage and the slurry containing precipitated crystal was taken out through the bottom portion of the vessel so as to maintain the slurry amount of 1.2 to 1.4 $m^3$ in the vessel. During the operation, the temperature in the vessel was kept at 40° C. by regulating the degree of depressurization and the agitation power was set on 1.8 kW/$m^3$.

The above-mentioned operation was continued for 24 hours from the start of feeding the starting raw material for crystallization, during which time continuous operation was possible without any trouble, including the pressure in the vessel of about 50 Torr. during steady period and the average heat load for the condenser of about 4000 kcal/hr.

The concentration of the crystal in the slurry which was continuously taken out was also stable at about 14% by weight. After the lapse of 24 hours, the feeding of the raw material was stopped, the pressure in the crystallizer was returned to atmospheric pressure, and the slurry was withdrawn through the bottom thereof. Then the inside of the crystallizer was observed. As a result, no crystal adhesion onto the inside wall was observed. The crystal was separated from the resultant slurry and recovered as 2,6-DMN having purity of 99.3%.

TABLE 4

Composition of starting raw material for crystallization (wt %)

|  | Example 7 | Example 8 | Example 18 |
|---|---|---|---|
| n-Heptane | 10.0 | 40.1 | — |
| Toluene | — | — | 10.0 |
| 2,6-DMN | 43.9 | 29.7 | 43.6 |
| 1,6-DMN | 37.0 | 25.0 | 37.1 |
| 1,5-DMN | 7.7 | 5.2 | 7.9 |
| Other DMN | 0.1 | 0.1 | 0.1 |
| Low boiling substances | 0.5 | 0.4 | 0.5 |
| High boiling substances | 0.8 | 0.5 | 0.8 |

EXAMPLE 9

Crystallizing operation was carried out by the use of the crystallizer which was used in Example 8 but was modified as follows. ① Instead of the vacuum pump, a gas circulator was installed to introduce the gas discharged therefrom into the crystallizer from the bottom portion; ② a gas disperser was installed at the bottom portion to uniformly disperse the introduced gas into the slurry in the crystallizer through 6 nozzles each having an inside diameter of 10 mm; and ③ the content in the crystallizer was cooled by evaporating n-heptane as the solvent through introduction of the gas.

There was used the same mixture as in Example 8 as the starting raw material for crystallization.

Firstly, the crystallizer was charged with 1.3 m$^3$ of n-heptane at about 40° C. as the solvent and nitrogen gas through the nozzles at the bottom portion. In a state that the crystallizer inside was kept at atmospheric pressure, approximately, the feed rate of nitrogen gas through the nozzles was gradually increased. When the feed rate reached 70 Nm$^3$/hr the feeding of the raw material kept at 65° C. was started at a feed rate of 200 kg/hour, which was kept constant during the crystallizing operation. The raw material was fed at a middle stage and the slurry containing precipitated crystal was taken out through the bottom portion of the vessel so as to maintain the slurry amount of 1.2 to 1.4 m$^3$ in the vessel. During the operation, the temperature in the vessel was kept at 40° C. by regulating the amount of nitrogen to be blown and the agitation power was set on 1.8 KW/m$^3$.

The above-mentioned operation was continued for 24 hours from the start of feeding the starting raw material for crystallization, during which time continuous operation was possible without any trouble, including the amount of nitrogen blown of about 70 Nm$^3$/hr during steady period and the average heat load for the solvent vapor condenser of about 4000 kcal/hr.

The concentration of the crystal in the slurry which was continuously taken out was also stable at about 14% by weight. After the lapse of 24 hours, the feeding of the raw material and the blowing of nitrogen were stopped, and the slurry was withdrawn through the bottom thereof. Then the inside of the crystallizer was observed. As a result, no crystal adhesion onto the inside wall was observed. The crystal was separated from the resultant slurry and recovered as 2,6-DMN having purity of 99.5%

EXAMPLE 10

Crystallizing operation was carried out by the use of the starting raw material for crystallization and the apparatus that are same as in Example 8 and liquefied propane as the solvent.

Firstly, the crystallizer was charged with 1.3 m$^3$ of n-heptane at about 60° C. and then n-heptane at 60° C. at a feed rate of 100 kg/hr at the middle portion thereof, while liquefied propane was fed therein through the nozzles at the bottom portion, during which time the content in the crystallizer was continuously taken out through the bottom portion thereof to maintain the volume of the liquid at 1.2 to 1.4 m$^3$. When the temperature in the crystallizer reached 40° C., the feeding of the raw material kept at 65° C. was started at a feed rate of 200 kg/hr, which was kept constant during the crystallizing operation. The feed rate of liquefied propane was regulated so as to keep the temperature of the content at 40° C., while the pressure in the crystallizer was maintained at atmospheric pressure, approximately. The slurry containing precipitated crystal was taken out through the bottom portion of the vessel so as to maintain the slurry amount of 1.2 to 1.4 m$^3$ in the vessel. During the operation, the agitation power was set on 1.8 kW/m$^3$.

The above-mentioned operation was continued for 24 hours from the start of feeding the starting raw material for crystallization, during which time continuous operation was possible without any trouble, including the feed rate of the liquefied propane of about 37 kg/hr.

The concentration of the crystal in the slurry which was continuously taken out was also stable at about 13% by weight. After the lapse of 24 hours, the feeding of the raw material and the liquefied propane was stopped, and the slurry was withdrawn through the bottom thereof. Then the inside of the crystallizer was observed. As a result, no crystal adhesion onto the inside wall was observed. The crystal was separated from the resultant slurry and recovered as 2,6-DMN having purity of 99.6%.

[First aspect of the invention: suppression of crystal agglomeration]

EXAMPLE 11

(1) Crystallization and crystal separation were carried out by the use of a tank-type crystallizer comprising a vertical cylindrical vessel which had an inside diameter of 1000 mm and a cylinder length of 2500 mm and was equipped with a stirrer; a cooling jacket; 4 baffle plates inside; and a thermometer inserted at the bottom portion thereof for monitoring the inside temperature, and by the use of a rotary vacuum filter (RVF) as the crystal separator. In brief, the starting raw material for crystallization was fed in the vessel at the top thereof. The slurry in the vessel was taken out therefrom at the bottom thereof and was sent with a pump, to the RVF, where the slurry was filtered and rinsed to afford crystal.

Specifically, the isomerization reaction product obtained by isomerizing 1,5-DMN which had been produced from o-xylene and butadiene was mixed with n-heptane as the solvent to form a mixture having chemical composition as given in Table 5, and the resultant mixture was used as the raw material.

At first, the crystallizer was charged with 0.6 m$^3$ of the raw material at 65° C. and gradually cooled inside by passing cooling water at 30° C. through the jacket as low as 40° C. over a period of 5 hours, under stirring of the content in the crystallizer. At the point of time when the inside temperature reached 40° C., continuous feeding of the starting raw material was started at a constant feed rate of 200 kg/hr, while the flow rate of cooling water was regulated so as to keep the temperature inside the crystallizer at 40° C. Simultaneously with the start of feeding the raw material in the crystallizer, the slurry therein was continuously taken out to filter it with the RVF. The volume of the slurry in the crystallizer was kept at 0.6 m$^3$ by controlling the number of revolutions of the RVF.

The average retention time of the raw material in the crystallizer was 2.6 hours. The agitation speed and agitation power in the crystallizer were set on 100 rpm, and 0.6 kW/m$^3$, respectively. With regard to the operation of the RVF, the cake was uniformly rinsed with n-heptane at 40° C. as the rising liquid at a feed rate of 30 kg/hr. The aforesaid operation of crystallization and crystal separation was continued for 72 hours, and the crystal discharged from the RVF was sampled at a prescribed time interval to examine the purity of 2,6-DMN in the resultant crystal. The relationship between the elapsed operation hour and the purity of 2,6-DMN is given in Table 7. The slurry concentration in the crystallizer during the operation was about 14% by weight, which was almost constant.

TABLE 5

Composition of starting raw material for crystallization (wt %)

| | Example 11 etc.* | Examples 19–20 |
|---|---|---|
| n-Heptane | 40.1 | — |
| Toluene | — | 40 |
| 2,6-DMN | 29.7 | 29.6 |
| 1,6-DMN | 25.0 | 25.0 |
| 1,5-DMN | 5.2 | 5.2 |
| Other DMN | 0.1 | 0.1 |
| Low boiling substances | 0.4 | 0.4 |
| High boiling substances | 0.5 | 0.5 |

*Example 11 etc. means Examples 11–17 and Comparative Example 4.

(2) The above-mentioned procedure was repeated to carry out crystallization and crystal separation except that the holdup amount in the crystallizer was set on 1.8 m$^3$, whereby the average retention time of the raw material is made to be 8 hours.

The slurry concentration in the crystallizer during the operation was about 14% by weight, which was almost constant. In the same manner as in the preceding item (1), the crystal discharged from the RVF was sampled at a prescribed time interval to examine the purity of 2,6-DMN in the resultant crystal. The relationship between the elapsed operation hour and the purity of 2,6-DMN is given in Table 7.

EXAMPLE 12

The procedure in Example 11 (2) was repeated to carry out crystallization and crystal separation except that the crystallizer which had been used in Example 11 was equipped with a circulation pump, which was used to take out the slurry in the crystallizer through the bottom and circulate the same to the top thereof at a flow rate of 2 m$^3$/hr. The circulation pump was an open impeller type centrifugal pump driven with a two pole 3.7 KW electric motor. The slurry concentration in the crystallizer during the operation was about 14% by weight, which was almost constant. In the same manner as in Example 11, the objective crystal was sampled at a prescribed time interval to examine the purity of 2,6-DMN in the crystal. The relationship between the elapsed operation hour and the purity of 2,6-DMN is given in Table 7.

EXAMPLE 13

The procedure in Example 11 (2) was repeated to carry out crystallization and crystal separation except that the agitation speed and agitation power in the crystallizer were set on 150 rpm, and 1.8 kW/m$^3$, respectively, whereby the thearetical power applied to the slurry was 3.4 times that in Example 11 (2). The slurry concentration in the crystallizer during the operation was about 14% by weight, which was almost constant. In the same manner as in Example 11, the objective crystal was sampled at a prescribed time interval to examine the purity of 2,6-DMN in the crystal. The relationship between the elapsed operation hour and the purity of 2,6-DMN is given in Table 7.

After the lapse of 48 hours from the start of the operation, a sample of crystal discharged from the RVF was collected for analysis. It contained 26% by weight of n-heptane. The chemical composition by weight of the cake from which n-heptane was removed is given in Table 6 (before reslurrying).

One part by weight of the crystal containing 26% by weight of n-heptane was dispersed in one part by weight of n-heptane at 20° C., and the resulting dispersion was filtered by suction with G2 filter (standard maximum diameter of opening of 100 to 150 µm). The chemical composition by weight of the crystal from which n-heptane was removed is given in Table 6 (after reslurrying). The amount of 2,6-DMN in the crystal obtained after this reslurrying was 86% based on the amount of 2,6-DMN in the cake which was dispersed in n-heptane. It can be seen that 2,6-DMN crystal having extremely high purity is obtained by reslurrying the crystal which is discharged from the RVF.

TABLE 6

| Composition (wt %) | Before reslurrying | After reslurrying |
|---|---|---|
| 2,6-DMN | 99.3 | 99.8 |
| 1,6-DMN | 0.3 | 0.1 |
| 1,5-DMN | 0.1 | 0.0 |
| Other DMN | 0.0 | 0.0 |
| Low boiling substances/ high boiling substances | 0.3 | 0.1 |

[First aspect of the invention: acceleration of crystal growth]

EXAMPLE 14

Crystallization and crystal separation were carried out by the use of a tank-type crystallizer comprising a vertical cylindrical vessel which had an inside diameter of 1000 mm and a cylinder length of 2500 mm and was equipped with a stirrer; a cooling jacket, 4 baffle plates inside; and a thermometer inserted at the bottom portion thereof for monitoring the inside temperature, and by using a rotary vacuum filter (RVF) as the crystal separator. In brief, the starting raw material for crystallization was fed in the vessel at the top thereof. The slurry in the vessel was taken out therefrom at the bottom thereof and was sent, in part, with a circulation pump to a double tube type heat exchanger, where the slurry was heated with steam from outside. Subsequently the slurry thus heated was returned to the crystallizer at the top thereof and cooled again. The balance of the slurry withdrawn from the crystallizer was fed with a pump, to the RVF, where the slurry was filtered and rinsed to afford crystal.

Specifically, the same composition as in Example 11 was used as the raw material.

At first, the crystallizer was charged with 1.8 m³ of the raw material at 65° C. and gradually cooled inside by passing cooling water at 30° C. through the jacket as low as 40° C. over a period of 5 hours, under stirring of the content in the crystallizer. At the point of time when the inside temperature reached 40° C., the slurry in the crystallizer was sent to the heat exchanger at a flow rate of 300 kg/hr by means of the circulation pump and was circulated through the crystallizer from the top thereof. Simultaneously therewith, the feeding of the raw material in the crystallizer was started at a constant feed rate of 200 kg/hr, and the slurry therein was continuously taken out to filter it with the RVF. The volume of the slurry in the crystallizer was kept at 1.8 m³ by controlling the number of revolutions of the RVF, and the inside temperature was kept at 40° C. by controlling the flow rate of the cooling water.

In the heat exchanger, the slurry was heated with steam, the feed rate of which was regulated so as to return the slurry at 45° C. to the crystallizer. Thereby recrystallization was effected through the circulation of the partially dissolved crystal to the top of the crystallizer, whereby the growth of crystal was accelerated.

The average retention time of the raw material in the crystallizer was 8 hours. The agitation speed and agitation power in the crystallizer were set on 100 rpm, and 0.6 kW/m³ respectively. With regard to the operation of the RVF, the cake was uniformly rinsed with n-heptane at 40° C. as the rising liquid at a feed rate of 30 kg/hr. The aforesaid operation of crystallization and crystal separation was continued for 72 hours, and the crystal discharged from the RVF was sampled at a prescribed time interval to examine the purity of 2,6-DMN in the resultant crystal. The relationship between the elapsed operation hour and the purity of 2,6-DMN is given in Table 7. The slurry concentration in the crystallizer during the operation was about 15% by weight, which was almost constant.

EXAMPLE 15

The double tube type heat exchanger and the circulation pump were removed from the equipment which had been used in Example 14. Instead, there were used, as seed crystal preparation tanks, two vertical cylindrical vessels which had each an inside diameter of 500 mm and a cylinder length of 1000 mm and were equipped with a stirrer, a cooling jacket and 4 baffle plates inside. By the use of the mixture having chemical composition same as in Example 11 as the starting raw-material and by using the aforesaid seed crystal preparation tanks, seed crystal was prepared from the raw material by the procedure comprising the steps of feeding 120 kg of the raw material in the form of liquid at 65° C. in the tanks, cooling the raw material under stirring by passing cooling water at 30° C. through the jacket, sufficiently reducing the cooling rate for the purpose of growing the crystal into effective seed crystal, cooling the raw material to 40° C. over a period of 8 hours, raising the temperature thereof to 45° C., and again cooling to 40° C. Thus there was prepared a slurry containing 18 kg of seed crystal by the above procedure.

Aside from the foregoing, the crystallizer was charged with 1.8 m³ of the raw material at 85° C. and cooled inside by passing cooling water at 30° C. through the jacket as low as 40° C. over a period of 5 hours, under stirring of the content in the crystallizer. At the point of time when the inside temperature reached 40° C., the feeding of the raw material in the crystallizer at 200 kg/hr was started, simultaneously with the feeding of the seed slurry thereinto at 10 kg/hr from the seed crystal preparation tanks. At the same time, the slurry in the crystallizer was continuously taken out to filter it with a RVF.

In the same manner as in Example 14, the amount of slurry and the crystallizer inside temperature were kept at 1.8 m³ and 40° C., respectively, and the operation of crystallization and crystal separation was continued for 72 hours. During the operation, one of the seed crystal preparation tanks was emptied every 12 hours, and thus the seed crystal withdrawal was switched from one another at every time of emptiness to continue the feeding of the seed crystal. In the same manner as in Example 14, the crystal discharged from the RVF was sampled at a prescribed time interval to examine the purity of 2,6-DMN in the crystal. The relationship between the elapsed operation hour and the purity of 2,6-DMN is given Table 7.

TABLE 7

| | Purity of 2,6-DMN (wt %) | | | | | | |
|---|---|---|---|---|---|---|---|
| Elapsed hour (hr) | 0 | 6 | 12 | 24 | 36 | 48 | 72 |
| Example 11 (1) | 99.6 | 99.4 | 99.3 | 99.3 | 99.2 | 99.4 | 99.2 |
| Example 11 (2) | 99.5 | 99.0 | 98.2 | 97.7 | 97.5 | 97.1 | 96.5 |
| Example 12 | 99.7 | 99.6 | 99.5 | 99.5 | 99.4 | 99.3 | 99.4 |
| Example 13 | 99.6 | 99.6 | 99.5 | 99.4 | 99.3 | 99.3 | 99.2 |
| Example 14 | 99.6 | 99.5 | 99.3 | 99.2 | 99.3 | 99.2 | 99.2 |
| Example 15 | 99.6 | 99.4 | 99.2 | 99.3 | 99.3 | 99.4 | 99.3 |
| Example 19 | 97.5 | 97.5 | 97.4 | 97.3 | 97.2 | 97.2 | 97.1 |
| Example 20 | 97.6 | 97.6 | 97.4 | 97.3 | 97.3 | 97.2 | 97.2 |

[Second aspect of the invention]

EXAMPLE 16

By cooling the starting raw material, which was the mixture having chemical composition same as in Example 11 to 40° C., there was prepared a filtration feedstock in the form of slurry with a crystal concentration of 15% by weight. 2,6-DMN crystal was separated from the filtration feedstock with a crystal concentration of 15% by weight using as a filter, a RVF compring a cylindrical filtering section of 100 mm in width and 300 mm in diameter, the surface of which was covered with a filter cloth; rinsing nozzles for cleaning filtered cake; and cleaning nozzles for cleaning the filter cloth after the cake peeling. The filtration was carried out by feeding the feedstock to the RVF at a constant rate of 1000 kg/hr; regulating the operational conditions such as the number of revolutions of the cylindrical filtering section and the degree of vacuum therein so as to attain a filtering treatment rate of 400 kg/hr; uniformly cleaning the filtered cake using n-heptane at 60° C. as the rinsing liquid at a constant flow rate of 80 kg/hr; and continuously cleaning the filter cloth using n-heptane at 40° C. as the liquid for cleaning the filter cloth after filtration at a constant flow rate of 30 kg/hr.

Steady operation was made possible after about 2 minutes from the start of the filtering operation, and was continued for 24 hours at the number of revolutions of 5 rpm and a degree of vacuum of 500 mm Hg, during which hours stable filtering treatment could be continued without causing filter cloth plugging up. The recovery rate of the crystal in filtration was about 92%. The crystal separated from the RVF by peeling was examined by optional sampling and analysis for purity during the course of the operation. As a result, the purity of 2,6-DMN excluding n-heptane was 99.0% or higher.

Comparative Example 4

The procedure in example 16 was repeated to try to carry out filtration except that the filter cloth cleaning was omitted.

As a result, filter cloth plugging took place in a short time from the start of the filtration, thus making it impossible to continue the filtration operation, since the treatment capacity of slurry filtration was limited to at most 100 kg/hr after the lapse of 30 minutes in spite of every possible adjustment of operational conditions of the RVF made to continue the operation.

EXAMPLE 17

The procedure in Example 16 was repeated to carry out filtration except that the filter cloth cleaning was carried out intermittently instead of continuously for 2 minutes at a time interval of 20 minutes each by the use of n-heptane at 70° C. instead of 30° C. at a flow rate of 30 kg/hr.

Steady operation was made possible after about 2 minutes from the start of the filtering operation, and was continued for 24 hours, during which hours stable filtering treatment could be continued without causing filter cloth plugging. The recovery rate of the crystal in filtration was about 92%. The crystal separated from the RVF by peeling was examined by optional sampling and analysis for purity during the course of the operation. As a result, the purity of 2,6-DMN excluding n-heptane was 99.0% or higher.

Since the same effect was realized in Example 17 in which the cleaning was carried out intermittently for 2 minutes at a time interval of 20 minutes as compared with Example 16 in which the cleaning was conducted continuously, it can be seen that the consumption of the liquid for cleaning the filter cloth could be decreased to 1/10 only by raising the temperature at the time of cleaning the filter cloth from 40° C. to 70° C.

First aspect of the invention: suppression of crystal adhesion

EXAMPLE 18

By the use of the same apparatus as in Example 7, crystallizing operation was carried out by using a mixture haivng chemical composition as given in Table 4 which mixture was obtained by mixing toluene with the isomerization reaction product obtained by isomerizing 1,5-DMN produced from o-xylene and butadiene. This mixture as the starting raw material for crystallization was fed in the crystallizer at 80° C. up to the overflow level and cooled with stirring to 60° C. When the temperature inside the crystallizer reached 60° C., the raw material at 80° C. was continuously fed therein from the bottom at a constant rate of 200 kg/hr, which was the starting time of crystallizing operation.

Simultaneously with the starting time, cooling water at 40° C. was passed through the jacket to cool the content in the crystallizer, the temperature of which was maintained at 60° C. by regulating the flow rate of the cooling water at 40° C. to be passed through the jacket. The content therein was mixed at an agitation power of 1.8 kW/m$^3$, and the slurry containing precipitated crystal was continuously taken out from the top portion as the overflow. The aforesaid operation was continued for 24 hours, during which time the cooling performance of the jacket and the cooling water flow rate of 0.16 m$^3$/hr in average were stabilized, enabling continuous operation without any trouble. The concentration of the crystal in the slurry which was continuously taken out by overflowing was also stable at about 12% by weight. After the lapse of 24 hours, the feeding of the raw material and the cooling water was stopped, and the slurry and cooling water were entirely withdrawn through the bottom of the crystallizer. Then, the inside of the vessel was observed. As a result, no crystal adhesion was observed even at the jacket fitted portion. The crystal was separated from the resultant slurry and recovered as 2,6-DMN having purity of 97.2%.

The above-mentioned procedure was repeated except that the cooling water temperature was set at 10° C. The Flow rate of the cooling water was 0.07 m$^3$/hr at the start of the crystallizing operation and was comparatively stable until 3 hours after the start. However, after the lapse of 3 hours from the start thereof, the flow rate of the cooling water began to increase because of lowered heat transfer performance, and after the lapse of 8 hours therefrom, the flow rate reached its upper limit of 5.0 m$^3$/hr. Thereafter the temperature inside the crystallizer began to rise because of the insufficient cooling capacity. Thus after the lapse of 8.5 hours therefrom, feeding of the raw material and the cooling water was stopped. Then the slurry and cooling water were entirely withdrawn through the bottom of the crystallizer, and the inside of the vessel was observed. As a result, there was observed crystal scale in a thickness of about 5 mm stuck to the jacket fitted portion.

[First aspect of the invention: suppression of crystal agglomeration]

EXAMPLE 19

By the use of the same apparatus as in Example 11, crystallization and crystal separation were carried out. The isomerization reaction product obtained by isomerizing 1,5-DMN which had been produced from o-xylene and butadiene was mixed with toluene as the solvent to form a mixture having chemical composition same as in Example 11, and the resultant mixture was used as the raw material.

At first, the crystallizer was charged with 0.6 m of the raw material at 65° C. and gradually cooled inside by passing cooling water at 30° C. through the jacket as low as 36° C. over a period of 5 hours, under stirring of the content in the crystallizer. At the point of time when the inside temperature reached 36° C., continuous feeding of the starting raw material was started at a constant feed rate of 200 kg/hr, while the flow rate of cooling water was regulated so as to keep the temperature inside the crystallizer at 36° C. Simultaneously with the start of feeding the raw material in the crystallizer, the slurry therein was continuously taken out to filter it with the RVF. The volume of the slurry in the crystallizer was kept at 0.6 m$^3$ by controlling the number of revolutions of the RVF.

The average retention time of the raw material in the crystallizer was 3.0 hours. The agitation speed and agitation power in the crystallizer were set on 100 rpm, and 0.8 kW/m$^3$, respectively. With regard to the operation of the RVF, the cake was uniformly rinsed with toluene at 40° C. as the rising liquid at a feed rate of 20 kg/hr. The aforesaid operation of crystallization and crystal separation was continued for 72 hours, and the crystal discharged from the RVF was sampled at a prescribed time interval to examine the purity of 2,6-DMN in the resultant crystal. The relationship between the elapsed operation hour and the purity of 2,6-DMN is given in Table 7. The slurry concentration in the crystallizer during the operation was about 14% by weight, which was almost constant.

[First aspect of the invention: acceleration of crystal growth]

EXAMPLE 20

By the use of the same apparatus and the same raw material as in Example 14, crystallization and crystal separation were carried out.

At first, the crystallizer was charged with 1.8 m$^3$ of the raw material at 65° C. and gradually cooled inside by passing cooling water at 30° C. through the jacket as low as 36° C. over a period of 5 hours, under stirring of the content in the crystallizer. At the point of time when the inside temperature reached 36° C., the slurry in the crystallizer was sent to the double tube type heat exchanger at a flow rate of 300 kg/hr by means of the circulation pump and was circulated through the crystallizer from top thereof. Simultaneously therewith, the feeding of the raw material in the crystallizer was started at a constant feed rate of 200 kg/hr, and the slurry therein was continuously taken out to filter it with the RVF. The volume of the slurry in the crystallizer was kept at 1.8 m³ by controlling the number of revolutions of the RVF, and the inside temperature was kept at 36° C. by controlling the flow rate of the cooling water.

In the heat exchanger, the slurry was heated with steam, the feed rate of which was regulated so as to return the slurry at 42° C. to the crystallizer. Thereby recrystallizaion was effected through the circulation of the partially dissolved crystal to the top of the crystallizer, whereby the growth of crystal was accelerated.

The average retention time of the raw material in the crystallizer was 9.5 hours. The agitation speed and agitation power in the crystallier were set on 100 rpm, and 0.8 kW/m³, respectively. With regard to the operation of the RVF, the cake was uniformly rinsed with n-heptane at 40° C. as the rising liquid at a feed rate of 20 kg/hr. The aforesaid operation of crystallization and crystal separation was continued for 72 hours, and the crystal discharged from the RVF was sampled at a prescribed time interval to examine the purity of 2,6-DMN in the resultant crystal. The relationship between the elapsed operation hour and the purity of 2,6-DMN is given in Table 7. The slurry concentration in the crystallizer during the operation was about 15% by weight, which was almost constant.

EXAMPLE 21

Acetic acid in an amount of 288.9 g was mixed with 3.2 g of water, 0.64 g of cobalt acetate quadrihydrate, 5.35 g of manganese acetate quadrihydrate, and 1.94 g of hydrogen bromide (47% aqueous solution) to prepare a catalyst solution. Then, 120.0 g of the above-prepared catalyst solution was fed in a 0.5 liter titanium-made autoclave (reactior) equipped with a stirrer, a reflux condenser and a raw material transfer pump. The balance 180.0 g of the catalyst solution was mixed with 30.0 g of the 2.6-dimethylnaphthalene (DMN) as obtained in Example 1. The resultant mixture was fed in a raw material feed tank and was heated to dissolve 2,6-DMN and prepare a raw material solution. The reaction system was pressurized with nitrogen gas to a regulated pressure of 18 kg/cm² G, and the content in the reactor was heated to 200° C. under stirrring. When the temperature and the pressure in the reactor were stabilized, the raw material solution and compressed air were fed in the reactor to start oxidation reaction. The raw material solution was continuously fed in the reactor over a period of one hour, while the flow rate of the feed air was regulated so that the concentration of oxygen in the exhaust gas was made to be 2% by volume. During the above period, the partial pressure of oxygen in the reactor was 0.12 kg/cm² (absolute pressure). After the feed of the raw material solution was finished, air was continuously fed for 9 minutes.

After the completion of the oxidation reaction, the reactor was cooled to room temperature, and the resultant reaction product was taken out from the reactor and filtered by suction with a glass filter to separate the filter cake in the form of crystal. Thereafter the cake thus separated was cleaned by rinsing with 80.0 g of acetic acid containing 20% by weight of water. The cake was weighted and subsequently dried with a dryer to afford 40.82 g of crude naphthalenedicarboxylic acid (NDCA) in the form of crystal. Thus the NDCA in the from of dried crystal was obtained in a purity of 96.8% by weight at a yield of 95.2 mol % based on the 2,6-DMN fed in the reaction system.

Comparative Example 5

DMN comprising as a principal component, 1,5-DMN which had been synthesized from o-xylene and butadiene as starting raw materials was incorporated with 2,7-DMN, MMN and TMN to form a DMN mixture, which was then isomerized in the presence of mordenite (produced by Tosoh Corporation) as the catalyst to afford a DMN isomerization reaction product. Subsequently 200 g of the DMN isomerization reaction product thus produced and 100 g of n-heptane were placed in a 400 mL glass container equipped with a stirrer under stirring and heating to 80° C. to form a solution, which was gradually cooled to 20° C. to precipitate crystal. The content in the glass container was filtered by suction with a G2 glass filter (standard maximum diameter of opening of 100 to 150 μm), and the crystal thus obtained was rinsed three times each with n-heptane at 0° C. In Table 8 are given the chemical compositions of the DMN isomerization reaction product (starting raw material for cyrstallization), of the crystal after filtration and of the crystal after every rinsing. It can be seen from the table that 1,6-DMN, 1,5-DMN and 1,7-DMN each contained in the impurities are steadily removed by every rinsing, whereas 2,7-DMN, MMN and TMN are difficult to remove by means of rinsing.

TABLE 8

|  | DMN | | | | | | | |
| --- | --- | --- | --- | --- | --- | --- | --- | --- |
|  | 2,6- | 1,6- | 1,5- | 2,7- | 1,7- | MMN | TMN | Total |
| Starting raw material | 29.15 | 32.05 | 11.01 | 7.58 | 3.22 | 4.58 | 12.41 | 100 |
| After filtration | 91.32 | 4.22 | 1.06 | 1.10 | 0.12 | 1.11 | 1.07 | 100 |
| After 1st rinsing | 95.46 | 1.81 | 0.46 | 0.67 | 0.03 | 0.82 | 0.76 | 100 |
| After 2nd rinsing | 97.08 | 0.71 | 0.17 | 0.58 | 0.00 | 0.73 | 0.73 | 100 |
| After 3rd rinsing | 97.70 | 0.22 | 0.09 | 0.58 | 0.00 | 0.72 | 0.69 | 100 |

What is claimed is:

1. A process for producing 2,6-dimethylnaphthalene which comprises crystallizing 2,6-dimethylnaphthalene from a mixture of dimethylnaphthalene isomers or a solution containing a mixture of dimethylnaphthalene isomers in a crystallizer, while suppressing crystal adhesion to the inside wall of the crystallizer, said mixture of dimethylnaphthalene isomers consisting essentially of an isomerization reaction product of 1,5-dimethylnaphthalene which is formed from o-xylene and butadiene each as a starting raw material, or of the isomerization reaction product of the mother liquor which is formed by separating 2,6-dimethylnaphthalene crystals from said isomerization reaction product of 1,5-dimethylnaphthalene, or of both of said isomerization reaction products, in the presence of at least one solvent selected from the group consisting of hexane, heptane, octane, isooctane, nonane, methylcyclopentane, cyclohexane, methylcyclohexane and decalin, wherein the mixture of dimethylnaphthalene isomers contains at most 10% by weight of 2,7-dimethylnaphthalene based on the entire amount of the dimethylnaphthalene series compounds, wherein the crystal adhesion to the inside wall of the crystallizer is suppressed by a method selected from the group consisting of (i) a method comprising concentrating a solution containing a mixture of dimethylnaphthalene isomers by depressurizing the crystallizer or treating a solution containing a mixture of dimethylnaphthalene isomers with an inert gas, thereby evaporating a solvent in the solution containing a mixture of dimethylnaphthaltene isomers; and (ii) a method comprising cooling a solution containing a mixture of dimethylnaphthalene isomers by introducing a liquefied gas into the solution, thereby evaporating the gas.

2. A process for producing 2,6-dimethylnaphthalene which comprises crystallizing 2,6-dimethylnaphthalene in a crystallizer from a mixture of dimethylnaphthalene isomers consisting essentially of the isomerization reaction product of 1,5-dimethylnaphthalene which is formed from o-xylene and butadiene each as a starting raw material, or of the isomerization reaction product of the mother liquor which is formed by separating 2,6-dimethylnaphthalene crystals from said isomerization reaction product of 1,5-dimethylnaphthalene, or of both the isomerization reaction products, in the presence of at least one solvent selected from the group consisting of hexane, heptane, octane, isooctane, nonane, methylcyclopentane, cyclohexane, methylcyclohexane and decalin, wherein the mixture of dimethylnaphthalene isomers contains at most 10% by weight of 2,7-dimethylnaphthalene based on the entire amount of the dimethylnaphthalene series compounds, and wherein crystal agglomeration is suppressed by a first method, a second method or the first method and the second method in combination; the first method comprising carrying out crystallization with an average retention time of the crystals in the crystallizer being at most 6 hours, the second method comprising destroying the agglomerate of the crystals by circulating slurry in the crystallizer by a circulation pump which is installed outside the crystallizer.

3. A process for producing 2,6-dimethylnapthalene which comprises crystallizing 2,6-dimethynaphthalene from a solution containing a mixture of dimethylnaphthalene isomers in a crystallizer, while accelerating crystal growth, said mixture of dimethylnaphthalene isomers consisting essentially of an isomerization reaction product of 1,5-dimethylnapthalene which is formed from o-xylene and butadiene each as a starting raw material, or of the isomerization reaction product of the mother liquor which is formed by seperating 2,6-dimethylnapthalene crystals from said isomerization reaction product of 1,5-dimethyllnaphthaleme, or of both of said isomerization reaction products, in the presence of at least one solvent selected from the group consisting of hexane, heptane, octane, isooctane, nonane, methylcyclopentane, cyclohexane, methylcyclohexane and decalin, wherein the mixture of dimethylnaphthalene isomers contains at most 10% by weight of 2,7-dimethylnaphthalene based on the entire amount of the dimethylnaphthalene series compounds, wherein the crystal growth is accelerated by dissolving part of the crystal, and recrystallizing the dissolved crystal, at least one time.

4. A process for producing 2,6-dimethylnaphthalene which comprises crystallizing 2,6-dimethylnaphthalene from a mixture of dimethylnaphthalene isomers consisting essentially of the isomerization reaction product of 1,5-dimethylnaphthalene which is formed from o-xylene and butadiene each as a starting raw material, or of the isomerization reaction product of the mother liquor which is formed by separating 2,6-dimethylnaphthalene crystals from said isomerization reaction product of 1,5-dimethylnaphthalene, or of both the isomerization reaction products in the presence of at least one solvent selected from the group consisting of hexane, heptane, octane, isooctane, nonane, methylcyclopentane, cyclohexane, methylcyclohexane and decalin, wherein the mixture of dimethylnaphthalene isomers contains at most 10% by weight of 2,7-dimethylnaphthalene based on the whole amount of the dimethylnaphthalene compounds, and wherein the crystallizing is carried out by crystallizing 2,6-dimethylnaphthalene to precipitate 2,6 dimethylnaphthalene crystals, filtering the 2,6-dimethylnaphthalene crystals in a filtering apparatus, separating the resultant filter cake from a filter cloth, and thereafter cleaning the filter cloth with the solvent used in the crystallization.

5. The process according to claim 4, wherein the temperature of the solvent for cleaning the filter cloth is not lower than the filtering temperature.

6. The process according to claim 4, wherein the filtering apparatus is a rotary vacuum filter.

7. A process for producing 2,6-dimethylnaphthalene which comprises crystallizing 2,6-dimethylnaphthalene from a mixture of dimethylnaphthalene isomers or a solution containing a mixture of dimethylnaphthalene isomers in a crystallizer, while suppressing crystal adhesion to the inside wall of the crystallizer, said mixture of dimethylnaphthalene isomers consisting essentially of an isomerization reaction product of 1,5-dimethylnaphthalene which is formed from o-xylene and butadiene each as a starting raw material, or of the isomerization reaction product of the mother liquor which is formed by separating 2,6-dimethylnaphthalene crystals from said isomerization reaction product of 1,5-dimethylnaphthalene, or of both of said isomerization reaction products, in the presence of at least one solvent selected from the group consisting of hexane, heptane, octane, isooctane, nonane, methylcyclopentane, cyclohexane, methylcyclohexane and decalin, wherein the mixture of dimethylnaphthalene isomers contains at most 5% by weight of 2,7-dimethylnaphthalene, at most 3% by weight of methylnaphthalene and at most 10% by weight of trimethylnaphthalene, each based on the entire amount of the dimethylnaphthalene series compounds, wherein the crystal adhesion to the inside wall of the crystallizer is suppressed by a method selected from the group consisting of (i) a method comprising concentrating a solution containing a mixture of dimethylnaphthalene isomers by depressurizing the crystallizer or treating a solution containing a mixture of dimethylnaphthalene isomers with an inert gas, thereby evaporating a solvent in the solution containing a mixture of dimethylnaphthalene isomers; and (ii) a method comprising cooling a solution containing a mixture of dimethylnaphthalene isomers by introducing a liquefied gas into the solution, thereby evaporating the gas.

8. A process for producing 2,6-dimethylnaphthalene which comprises crystallizing 2,6-dimethylnaphthalene from a solution containing a mixture of dimethylnaphthalene isomers in a crystallizer, while accelerating crystal growth, said mixture of dimethylnaphthalene isomers consisting essentially of an isomerization reaction produce of 1,5-dimethylnaphthalene which is formed from o-xylene and butadiene each as a starting raw material, or of the isomerization reaction product of the mother liquor which is formed by separating 2,6-dimethylnaphthalene crystals from said isomerization reaction product of 1,5-dimethylnaphthalene, or of both of said isomerization reaction products, in the presence of at least one solvent selected from the group consisting of hexane, heptane, octane, isooctane, nonane, methylcyclopentane, cyclohexane, methylcyclohexane and decalin, wherein the mixture of dimethylnaphthalene isomers contains at most 5% by weight of 2,7-dimethylnaphthalene, at most 3% by weight of methylnaphthalene and at most 10% by weight of trimethylnaphthalene, each based on the entire amount of the dimethylnaphthalene series compounds, wherein the crystal growth is accelerated by dissolving part of the crystal, and recrystallizing the dissolved crystal, at least one time.

9. A process for producing 2,6-dimethylnaphthalene which comprises crystallizing 2,6-dimethylnaphthalene in a crystallizer from a mixture of dimethylnaphthalene isomers consisting essentially of an isomerization reaction product of 1,5-dimethylnaphthalene which is formed from o-xylene and butadiene each as a starting raw material, or of the isomerization reaction product of the mother liquor which is formed by separating 2,6-dimethylnaphthalene crystals from said isomerization reaction product of 1,5-dimethylnaphthalene, or of both of said isomerization reaction products, in the presence of at least one solvent selected from the group consisting of hexane, heptane, octane, isooctane, nonane, methylcyclopentane, cyclohexane, methylcyclohexane and decalin, wherein the mixture of dimethylnaphthalene isomers contains at most 5% by weight of 2,7-dimethylnaphthalene, at most 3% by weight of methylnaphthalene and at most 10% by weight of trimethylnaphthalene, each based on the entire amount of the dimethylnaphthalene series compounds, and wherein crystal agglomeration is suppressed by a first method, a second method or the first method and the second method in combination; the first method comprising carrying out crystallization with an average retention time of the crystals in the crystallizer being at most 6 hours; the second method comprising destroying the agglomerate of the crystals by circulating slurry in the crystallizer by a circulation pump which is installed outside the crystallizer.

10. A process for producing 2,6-dimethylnaphthalene which comprises crystallizing 2,6-dimethylnaphthalene from a mixture of dimethylnaphthalene isomers consisting essentially of an isomerization reaction product of 1,5-dimethylnaphthalene which is formed from o-xylene and butadiene each as a starting raw material, or of the isomerization reaction product of the mother liquor which is formed by separating 2,6-dimethylnaphthalene crystals from said isomerization reaction product of 1,5-dimethylnaphthalene, or of both of said isomerization reaction products, in the presence of at least one solvent selected from the group consisting of hexane, heptane, octane, isooctane, nonane, methylcyclopentane, cyclohexane, methylcyclohexane and decalin, wherein the mixture of dimethylnaphthalene isomers contains at most 5% by weight of 2,7-dimethylnaphthalene, at most 3% by wweight of methylnaphthalene and at most 10% by weight of trimethylnaphthalene, each based on the entire amount of the dimethylnaphthalene, series compounds, and wherein the crystallizing is carried out by crystallizing 2,6-dimethylnaphthalene to precipitate 2,6-dimethylnaphthalene crystals, filtering the 2,6-dimethylnaphthalene crystals in a filtering apparatus, separating the resultant filter cake from a filter cloth, and thereafter cleaning the filter cloth with the solvent used in the crystallization.

11. The process according to claim 10, wherein the temperature of the solvent for cleaning the filter cloth is not lower than a filtering temperature.

12. The process according to claim 10, wherein the filtering apparatus is a rotary vacuum filter.

13. A process for producing 2,6-dimethylnaphthalene which comprises crystallizing 2,6-dimethylnaphthalene from a mixture of dimethylnaphthalene isomers or a solution containing a mixture of dimethylnaphthalene isomers in a crystallizer, while suppressing crystal adhesion to the inside wall of the crystallizer, said mixture of dimethylnaphthalene isomers consisting essentially of an isomerization reaction product of 1,5-dimethylnaphthalene which is formed from o-xylene and butadiene each as a starting raw material, or of the isomerization reaction product of the mother liquor which is formed by separating 2,6-dimethylnaphthalene crystals from said isomerization reaction product of 1,5-dimethylnaphthalene, or of both of said isomerization reaction products, in the presence of at least one solvent selected from the group consisting of hexane, heptane, octane, isooctane, nonane, methylcyclopentane, cyclohexane, methylcyclohexane and decalin, wherein the mixture of dimethylnaphthalene isomers contains at most 10% by weight of 2,7-dimethylnaphthalene, based on the entire amount of the dimethylnaphthalene series compounds, wherein the crystal adhesion to the inside wall of the crystallizer is suppressed by equipping the crystallizer with a heat transfer surface and passing a coolant to be in contact with the heat transfer surface, wherein the difference between the temperature of the coolant and the temperature of the mixture of dimethylnaphthalene isomers or a solution containing the mixture of dimethylnaphthalene isomers is maintained at 40° C. or less.

14. The process according to claim 13, wherein the mixture of dimethylnaphthalene isomers contains at most 5% by weight of 2,7-dimethylnaphthalene, at most 3% by weight of methylnaphthalene and at most 10% by weight of trimethylnaphthalene, each based on the entire amount of the dimethylnaphthalene series compounds.

15. A process for producing 2,6-dimethylnaphthalene which comprises crystallizing 2,6-dimethylnaphthalene from a solution containing a mixture of dimethylnaphthalene isomers in a crystallizer, while accelerating crystal growth, said mixture of dimethylnaphthalene isomers consisting essentially of an isomerization reaction product of 1,5-dimethylnaphthalene which is formed from o-xylene and butadiene each as a starting raw material, or of the isomerization reaction product of the mother liquor which is formed by separating 2,6-dimethylnaphthalene crystals from said isomerization reaction product of 1,5-dimethylnaphthalene, or of both of said isomerization reaction products, in the presence of at least one solvent selected from the group consisting of hexane, heptane, octane, isooctane, nonane, methylcyclopentane, cyclohexane, methylcyclohexane and decalin, wherein the mixture of dimethylnaphthalene isomers contains at most 5% by weight of 2,7-dimethylnaphthalene based on the entire amount of the dimethylnaphthalene series compounds, wherein the crystal growth is accelerated by separately preparing a 2,6-dimethylnaphthalene crystal which is added as a seed crystal in the crystallizer.

16. The process according to claim 15, wherein the mixture of dimethylnaphthalene isomers contains at most 5% by weight of 2,7-dimethylnaphthalene, at most 3% by weight of methylnaphthalene and at most 10% by weight of trimethylnaphthalene, each based on the entire amount of the dimethylnaphthalene series compounds.

17. A process for producing 2,6-dimethylnaphthalene which comprises crystallizing 2,6-dimethylnaphthalene in a crystallizer from a mixture of dimethylnaphthalene isomers consisting essentially of an isomerization reaction product of 1,5-dimethylnaphthalene which is formed from o-xylene and butadiene each as a starting raw material, or of the isomerization reaction product of the mother liquor which is formed by separating 2,6-dimethylnaphthalene crystals from said isomerization reaction product of 1,5-dimethylnaphthalene, or of both of said isomerization reaction products, in the presence of at least one solvent selected from the group consisting of hexane, heptane, octane, isooctane, nonane, methylcyclopentane, cyclohexane, methylcyclohexane and decalin, wherein the mixture of dimethylnaphthalene isomers contains at most 5 by weight of 2,7-dimethylnaphthalene based on the entire amount of the dimethylnaphthalene series compounds, and wherein crystal agglomeration is suppressed by stirring the contents in the crystallizer to an extent that the crystal agglomeration is suppressed.

18. The process according to claim 17, wherein the mixture of dimethylnaphthalene isomers contains at most 5% by weight of 2,7-dimethylnaphthalene, at most 3% by weight of methylnaphthalene and at most 10% by weight of trimethylnaphthalene, each based on the entire amount of the dimethylnaphthalene series compounds.

* * * * *